(12) United States Patent
Noguchi

(10) Patent No.: US 11,771,400 B2
(45) Date of Patent: Oct. 3, 2023

(54) ULTRASOUND DIAGNOSTIC APPARATUS AND METHOD OF CONTROLLING ULTRASOUND DIAGNOSTIC APPARATUS

(71) Applicant: FUJIFILM Corporation, Tokyo (JP)

(72) Inventor: Masafumi Noguchi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 969 days.

(21) Appl. No.: 16/548,418

(22) Filed: Aug. 22, 2019

(65) Prior Publication Data

US 2020/0100763 A1    Apr. 2, 2020

(30) Foreign Application Priority Data

Sep. 27, 2018   (JP) .................................. 2018-182428

(51) Int. Cl.
     *A61B 8/00*      (2006.01)
     *A61B 8/08*      (2006.01)
     (Continued)

(52) U.S. Cl.
CPC ............ *A61B 8/0891* (2013.01); *A61B 8/085* (2013.01); *A61B 8/0875* (2013.01); *A61B 8/13* (2013.01);
(Continued)

(58) Field of Classification Search
CPC ......... A61B 8/14; A61B 8/085; A61B 8/0891; A61B 8/485; G06T 7/0016
See application file for complete search history.

(56) References Cited

U.S. PATENT DOCUMENTS

| | | | |
|---|---|---|---|
| 6,659,953 B1 * | 12/2003 | Sumanaweera | ......... G06T 7/246 600/443 |
| 2008/0269605 A1 | 10/2008 | Nakaya | |

(Continued)

FOREIGN PATENT DOCUMENTS

| | | |
|---|---|---|
| JP | 2008-272025 A | 11/2008 |
| JP | 2017-12598 A | 1/2017 |

OTHER PUBLICATIONS

Extended European Search Report for European Application No. 19191121.3, dated Jan. 24, 2020.

(Continued)

*Primary Examiner* — Rajeev P Siripurapu
(74) *Attorney, Agent, or Firm* — Birch, Stewart, Kolasch & Birch, LLP

(57) ABSTRACT

An ultrasound diagnostic apparatus includes an ultrasound probe, a reference image holding unit that holds an ultrasound image acquired by fixing the position of the ultrasound probe as a reference image, a movement vector calculation unit that calculates a movement vector between two ultrasound images, a movement vector integration unit that integrates the movement vectors from the time when the reference image is held until the current time, a deformed image generation unit that generates a deformed image in which the reference image is moved and changed on the basis of an integration result, a tomographic plane determination unit that compares the deformed image with the current ultrasound image, to determine whether or not tomographic planes of the reference image and the current ultrasound image are the same as each other, and a determination result notification unit that notifies a user of a determination result.

19 Claims, 10 Drawing Sheets

(51) Int. Cl.
    *G06T 7/246*     (2017.01)
    *A61B 8/13*     (2006.01)
    *G06T 7/00*     (2017.01)

(52) U.S. Cl.
    CPC ............... *A61B 8/46* (2013.01); *A61B 8/485* (2013.01); *A61B 8/5246* (2013.01); *A61B 8/54* (2013.01); *G06T 7/0016* (2013.01); *G06T 7/248* (2017.01); *G06T 2207/10132* (2013.01); *G06T 2207/30101* (2013.01)

(56) References Cited

U.S. PATENT DOCUMENTS

| | | |
|---|---|---|
| 2012/0253195 A1 | 10/2012 | Inoue et al. |
| 2014/0288425 A1* | 9/2014 | Shin ................ G06T 7/0016 600/438 |
| 2017/0196532 A1 | 7/2017 | Choi |
| 2021/0128099 A1* | 5/2021 | Al-Noor ................ A61B 8/461 |

OTHER PUBLICATIONS

European Office Acton dated Sep. 11, 2020 for Application No. 19 191 121.3.

* cited by examiner

ULTRASOUND DIAGNOSTIC APPARATUS AND METHOD OF CONTROLLING ULTRASOUND DIAGNOSTIC APPARATUS

CROSS-REFERENCE TO RELATED APPLICATIONS

The present application claims priority under 35 U.S.C. § 119 to Japanese Patent Application No. 2018-182428, filed on Sep. 27, 2018. Each of the above application(s) is hereby expressly incorporated by reference, in its entirety, into the present application.

BACKGROUND OF THE INVENTION

1. Field of the Invention

The present invention relates to an ultrasound diagnostic apparatus and a method of controlling an ultrasound diagnostic apparatus, and particularly, to an ultrasound diagnostic apparatus and a method of controlling an ultrasound diagnostic apparatus that are used for a compression test of a subject.

2. Description of the Related Art

From the past, ultrasound diagnostic apparatuses have been known as apparatuses that obtain images of the inside of a subject. Generally, the ultrasound diagnostic apparatus comprises an ultrasound probe provided with an oscillator array in which a plurality of elements are arranged. In a state where the ultrasound probe is brought into contact with a body surface of a subject, an ultrasound beam is transmitted from the oscillator array toward the inside of the subject, ultrasonic echoes from the subject are received in the oscillator array, and element data are acquired. Moreover, the ultrasound diagnostic apparatuses process the obtained element data electrically, and generate an ultrasound image for a relevant part of the subject.

It is generally performed that a blood vessel of the subject is observed using such ultrasound diagnostic apparatuses, and the presence or absence of a thrombus within the blood vessel is inspected. As a disease related to the thrombus in the blood vessel, for example, so-called deep-vein thrombosis (DVT) is known. The DVT is a disease in which a thrombus occurs in a deep vein, and is often generated in a lower thigh.

Although a normal deep vein in which a thrombus is not present is easily deformed by compression, the deep vein in which the thrombus has occurred is not easily deformed due to the compression. Therefore, as a method of inspecting the DVT that has occurred in the lower thigh using the ultrasound diagnostic apparatuses, for example, a so-called compression test method of observing a cross-section of the compressed deep vein while compressing the deep vein with a concern that the DVT may occur is known.

In the ultrasound diagnostic apparatus, various measures are made in order to accurately perform such a compression test. For example, in order to easily observe the deformation of the deep vein, JP2008-272025A discloses an ultrasound diagnostic apparatus that automatically specifies an ultrasound image in which the contact pressure between an ultrasound probe and a subject is maximized, and an ultrasound image in which a deep vein is not deformed by a compression test, and displays these ultrasound images side by side.

SUMMARY OF THE INVENTION

Meanwhile, an observation target, such as a blood vessel, is usually compressed by pressing the ultrasound probe against a body surface of the subject in the compression test. However, in this case, inclination, position, and the like of the ultrasound probe may shift. In this case, even in a case where the ultrasound diagnostic apparatus disclosed in JP2008-272025A is used, there are problems in that accurate diagnosis is difficult such that different tomographic planes may be observed before and after the compression, and a thrombus that is locally present within a blood vessel may be overlooked.

The invention has been made in order to solve such related-art problems, and an object thereof is to provide an ultrasound diagnostic apparatus and a method of controlling an ultrasound diagnostic apparatus that allow a user to perform accurate diagnosis in a compression test.

In order to achieve the above object, an ultrasound diagnostic apparatus of the invention is an ultrasound diagnostic apparatus that has an ultrasound probe and is used to compression-test an observation target within a subject by pressing the ultrasound probe against a body surface of the subject, the ultrasound diagnostic apparatus comprising: an image acquisition unit that performs transmission of an ultrasound beam from the ultrasound probe toward the subject and acquires ultrasound images consecutively and sequentially; a display unit that displays the ultrasound image acquired by the image acquisition unit; a reference image holding unit that holds the ultrasound image acquired by the image acquisition unit as a reference image in a state where a position of the ultrasound probe is fixed in order to depict a tomographic plane of the observation target on the display unit; a movement vector calculation unit that calculates a movement vector indicating an image movement change between two ultrasound images that are consecutive for each predetermined number of frames among the ultrasound images sequentially acquired by the image acquisition unit; a movement vector integration unit that integrates the movement vectors that are respectively calculated by the movement vector calculation unit in the ultrasound images from the time when the reference image is held by the reference image holding unit until the current time; a deformed image generation unit that generates a deformed image in which the ultrasound image held as the reference image by the reference image holding unit is moved and changed until the current time on the basis of the movement change integrated by the movement vector integration unit; a tomographic plane determination unit that determines whether or not a tomographic plane of the subject depicted from the reference image and a tomographic plane of the subject depicted from the ultrasound image of the current frame are the same as each other by comparing the deformed image generated by the deformed image generation unit with the ultrasound image of the current frame acquired by the image acquisition unit; and a determination result notification unit that notifies a user of a determination result caused by the tomographic plane determination unit.

The movement vector calculation unit can calculate a movement change of each pixel in the ultrasound image as the movement vector.

In this case, it is preferable that the movement vector integration unit integrates the movement vectors for each pixel with respect to the ultrasound images of a plurality of frames acquired by the image acquisition unit, and the deformed image generation unit generates the deformed image by moving and changing each pixel in the reference image until the current time in accordance with the movement change integrated by the movement vector integration unit.

Alternatively, the movement vector calculation unit can also calculate a movement change of a high-luminance pixel of which a luminance is equal to or more than a predetermined threshold, among all pixels in the ultrasound image, as the movement vector.

In this case, it is preferable that the movement vector integration unit integrates the movement vectors for each high-luminance pixel with respect to the ultrasound images of a plurality of frames acquired by the image acquisition unit, and the deformed image generation unit generates the deformed image on the basis of a movement change of each high-luminance pixel in the reference image.

Alternatively, the movement vector calculation unit can partition the ultrasound images adjacent to each other in time series into a predetermined number of regions, respectively, and calculate a movement change of one pixel in each of the regions as the movement vector of the region.

In this case, it is preferable that the movement vector integration unit integrates the movement vectors for each of the regions partitioned by the movement vector calculation unit in the ultrasound images of the plurality of frames acquired by the image acquisition unit, and the deformed image generation unit generates the deformed image on the basis of a movement change of each region in the reference image.

Moreover, the tomographic plane determination unit can compare the deformed image with the ultrasound image of the current frame for each of the regions partitioned by the movement vector calculation unit, to determine the tomographic planes of the subject, and the determination result notification unit can notify the user of the determination result for each partitioned region caused by the tomographic plane determination unit.

Additionally, the tomographic plane determination unit can perform image analysis with respect to the deformed image and the ultrasound image of the current frame, to calculate a similarity between the deformed image and the ultrasound image of the current frame, and can determine the tomographic planes of the subject on the basis of the calculated similarity.

In this case, the determination result notification unit can superimpose the determination result caused by the tomographic plane determination unit on the ultrasound image of the current frame to display the superimposed image on the display unit.

Additionally, the ultrasound diagnostic apparatus can further comprise a mask image generation unit that performs image analysis with respect to the deformed image generated by the deformed image generation unit, and the ultrasound image of the current frame acquired by the image acquisition unit to detect at least one of muscle fibers or a bone, and generates a mask image in which regions other than the muscle fibers and the bone detected with respect to the deformed image and the ultrasound image of the current frame are masked.

In this case, it is preferable that the tomographic plane determination unit determines the tomographic planes of the subject by comparing the mask image for the deformed image and the mask image for the ultrasound image of the current frame.

Alternatively, it is preferable that the ultrasound diagnostic apparatus further comprises a mask image generation unit that performs image analysis with respect to the ultrasound images, which are consecutively and sequentially acquired by the image acquisition unit to detect at least one of muscle fibers or a bone, and generates a mask image in which regions other than the muscle fibers and the bone detected with respect to the ultrasound image are masked, the reference image holding unit holds the mask image generated by the mask image generation unit at the time when the position of the ultrasound probe is fixed in order to depict a tomographic plane of the observation target on the display unit, as the reference image, the movement vector calculation unit calculates an image movement change in the mask image as the movement vector, and the deformed image generation unit generates a deformed image in which the mask image held as the reference image by the reference image holding unit is moved and changed until the current time on the basis of a movement change of at least one of the muscle fibers or the bone integrated by the movement vector integration unit.

In this case, it is preferable that the tomographic plane determination unit determines a tomographic plane of the subject by comparing the deformed image with a mask image that is masked with respect to the ultrasound image of the current frame by the mask image generation unit.

Additionally, the ultrasound diagnostic apparatus can further comprise an input unit that allows a user to perform an input operation; and a trigger signal transmitting unit that transmits a trigger signal to the reference image holding unit and the movement vector integration unit in a case where information indicating that the trigger signal instructing to start a new operation is transmitted is input by the user via the input unit.

Alternatively, the ultrasound diagnostic apparatus further comprises a trigger signal transmitting unit that performs image analysis with respect to the ultrasound images acquired consecutively and sequentially by the image acquisition unit to calculate an image change amount that is at least one of an image movement distance between the two consecutive ultrasound images or a rotational amount between the two consecutive ultrasound images, and transmits a trigger signal instructing to start a new operation to the reference image holding unit and the movement vector integration unit in a case where the ultrasound images of which the image change amount is equal to or less than a predetermined threshold are consecutively acquired by a predetermined number of frames.

Additionally, the display unit can display the deformed image side by side with the ultrasound image of the current frame.

A method of controlling an ultrasound diagnostic apparatus is a method of controlling an ultrasound diagnostic apparatus that is used to compression-test an observation target within a subject by pressing an ultrasound probe against a body surface of the subject. The method comprises performing transmission of an ultrasound beam toward the subject and acquiring ultrasound images consecutively and sequentially; holding an ultrasound image as a reference image in a state where a position of the ultrasound probe is fixed in order to depict a tomographic plane of the observation target; calculating a movement vector indicating an image movement change between two ultrasound images that are consecutive for each predetermined number of frames among the sequentially acquired ultrasound images; integrating the movement vectors that are respectively calculated in the ultrasound images from the time when the reference image is held to the current time; generating a deformed image in which the ultrasound image held as the reference image on the basis of the integrated movement change is moved and changed until the current time; determining whether or not a tomographic plane of the subject depicted from the reference image and a tomographic plane of the subject depicted from the ultrasound image of the current frame are the same as each other by comparing the generated deformed image with the acquired ultrasound image of the current frame; and notifying a user of a determination result.

According to the invention, the ultrasound diagnostic apparatus further comprises the reference image holding unit that holds the ultrasound image acquired by the image acquisition unit as the reference image in a state where the position of the ultrasound probe is fixed in order to depict the tomographic plane of the observation target on the display unit; the movement vector calculation unit that calculates the movement vector indicating the image movement change between the two ultrasound images that are consecutive for each predetermined number of frames among the ultrasound images sequentially acquired by the image acquisition unit; the movement vector integration unit that integrates the movement vectors that are respectively calculated by the movement vector calculation unit in the ultrasound images from a frame corresponding to the reference image held by the reference image holding unit to the current frame that is acquired by the image acquisition unit; the deformed image generation unit that generates the deformed image in which the ultrasound image held as the reference image by the reference image holding unit is moved and changed until the current time on the basis of the movement change integrated by the movement vector integration unit; the tomographic plane determination unit that determines whether or not the tomographic plane of the subject depicted from the reference image and the tomographic plane of the subject depicted from the ultrasound image of the current frame are the same as each other by comparing the deformed image generated by the deformed image generation unit with the ultrasound image of the current frame acquired by the image acquisition unit; and the determination result notification unit that notifies the user of the determination result caused by the tomographic plane determination unit. Therefore, the user can perform an accurate diagnosis in the compression test.

DESCRIPTION OF THE PREFERRED EMBODIMENTS

Hereinafter, embodiments of the invention will be described on the basis of the accompanying drawings.

Embodiment 1

Figure 1:
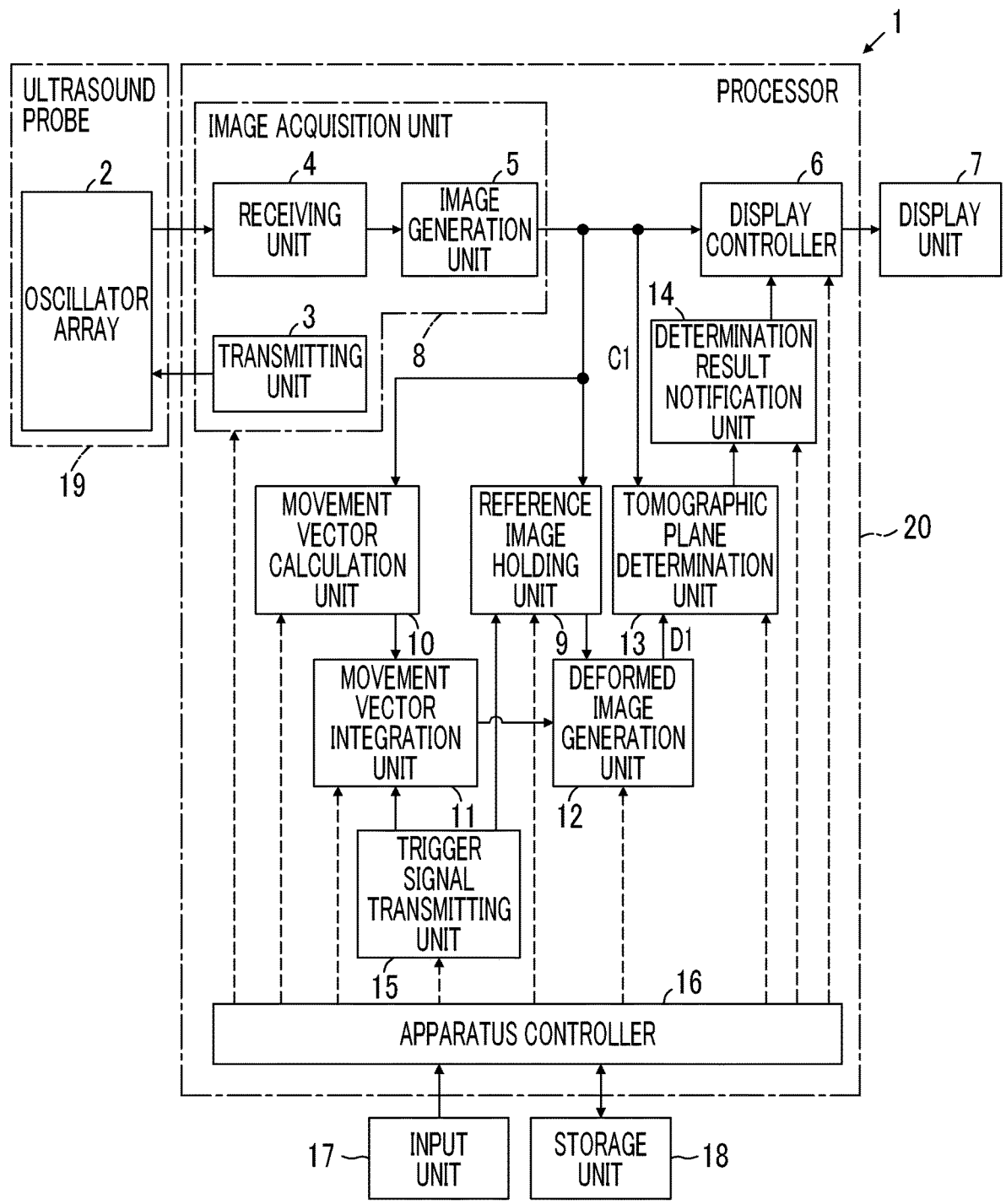
FIG. 1 is a block diagram illustrating the configuration of an ultrasound diagnostic apparatus related to Embodiment 1 of the invention.

The configuration of an ultrasound diagnostic apparatus 1 related to Embodiment 1 of the invention is illustrated in FIG. 1. As illustrated in FIG. 1, the ultrasound diagnostic apparatus 1 comprises an oscillator array 2, and a transmitting unit 3 and a receiving unit 4 are connected to the oscillator array 2, respectively. An image generation unit 5, a display controller 6, and a display unit 7 are sequentially connected to the receiving unit 4. Here, an image acquisition unit 8 is configured by the transmitting unit 3, the receiving unit 4, and the image generation unit 5. Additionally, a reference image holding unit 9 and a movement vector calculation unit 10 are connected to the image generation unit 5, and a movement vector integration unit 11 is connected to the movement vector calculation unit 10. Additionally, a deformed image generation unit 12 is connected to the reference image holding unit 9 and the movement vector integration unit 11, and a tomographic plane determination unit 13 is connected to the deformed image generation unit 12. Additionally, the image generation unit 5 and a determination result notification unit 14 are connected to the tomographic plane determination unit 13, and the display controller 6 is connected to the determination result notification unit 14. Additionally, a trigger signal transmitting unit 15 is connected to the reference image holding unit 9 and the movement vector integration unit 11.

Moreover, an apparatus controller 16 is connected the display controller 6, the image acquisition unit 8, the reference image holding unit 9, the movement vector calculation unit 10, the movement vector integration unit 11, the deformed image generation unit 12, the tomographic plane determination unit 13, the determination result notification unit 14, and the trigger signal transmitting unit 15, and an input unit 17 and a storage unit 18 are connected to the apparatus controller 16. Here, the apparatus controller 16 and the storage unit 18 are connected to each other so as to be capable of transferring information bidirectionally.

Additionally, the oscillator array 2 is included in the ultrasound probe 19, and a processor 20 is configured by the display controller 6, the image acquisition unit 8, the reference image holding unit 9, the movement vector calculation unit 10, the movement vector integration unit 11, the deformed image generation unit 12, the tomographic plane determination unit 13, the determination result notification unit 14, the trigger signal transmitting unit 15, and the apparatus controller 16.

The oscillator array 2 of the ultrasound probe 19 illustrated in FIG. 1 has a plurality of oscillators arranged in one dimension or two dimensions. These oscillators transmit ultrasonic waves in accordance with drive signals supplied from the transmitting unit 3, respectively, and receive the ultrasonic echoes from the subject to output the received signals. The respective oscillators are configured by forming electrodes to both ends of piezoelectric bodies, such as piezoelectric ceramic represented by lead zirconate titanate (PZT), polymeric piezoelectric elements represented by polyvinylidene difluoride (PVDF), and piezoelectric single crystals represented by a lead magnesium niobate-lead titanate solid solution (PMN-PT).

The transmitting unit 3 of the image acquisition unit 8 includes, for example, a plurality of pulse generators, and adjust the amounts of delay of the respective drive signals to supply the adjusted amounts of delay to the plurality of oscillators such that the ultrasonic waves transmitted from the plurality of oscillators of the oscillator array 2 form an ultrasound beam, on the basis of a transmission delay pattern selected depending on a control signal from the apparatus controller 16. In this way, in a case where pulsed or consecutive wave-like voltages are applied to electrodes of the plurality of oscillators of the oscillator array 2, piezoelectric bodies expand and contract, pulsed or consecutive wave-like ultrasonic waves are generated from the respective oscillators, and an ultrasound beam is formed from a synthetic wave of the ultrasonic waves.

The transmitted ultrasound beam is reflected in, for example, targets, such as a part of the subject, and is propagated toward the oscillator array 2 of the ultrasound probe 19. The ultrasonic echoes propagated toward the oscillator array 2 in this way are received by the respective oscillators that constitute the oscillator array 2. In this case, the respective oscillators that constitute the oscillator array 2 expand and contract by receiving the propagating ultrasonic echoes, to generate electrical signals, and output the electrical signals to the receiving unit 4.

Figure 2:
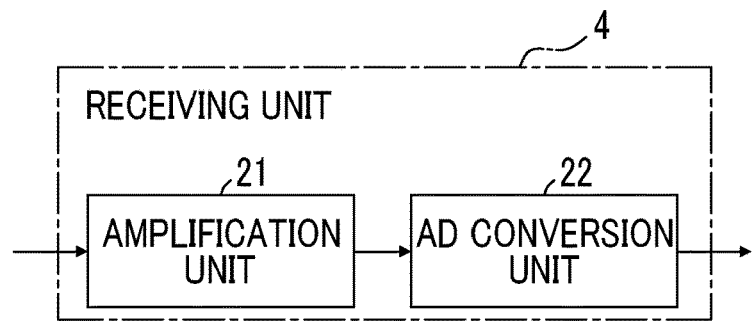
FIG. 2 is a block diagram illustrating an internal configuration of a receiving unit in Embodiment 1 of the invention.

The receiving unit 4 of the image acquisition unit 8 processes the received signals output from the oscillator array 2 in accordance with the control signal from the apparatus controller 16. As illustrated in FIG. 2, the receiving unit 4 has a configuration in which an amplification unit 21 and an analog-digital (AD) conversion unit 22 are serially connected. The amplification unit 21 amplifies the received signals input from the respective oscillators that constitute the oscillator array 2, and transmits the amplified received signals to the AD conversion unit 22. AD conversion unit 22 converts the received signals transmitted from the amplification unit 21 into digitalized data, and sends the data to the image generation unit 5 of the image acquisition unit 8.

Figure 3:
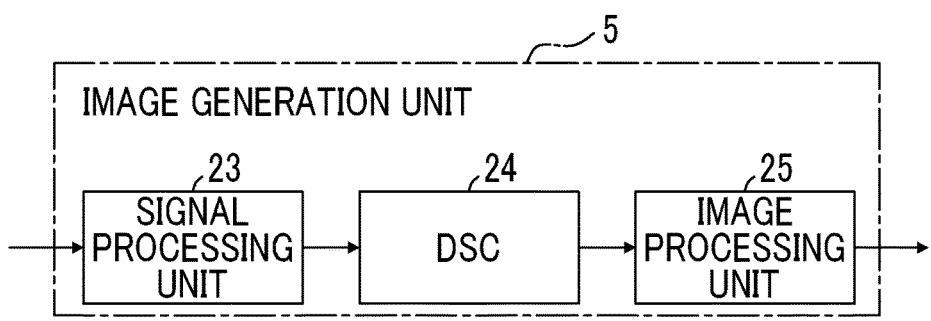
FIG. 3 is a block diagram illustrating an internal configuration of an image generation unit in Embodiment 1 of the invention.

As illustrated in FIG. 3, the image generation unit 5 of the image acquisition unit 8 has a configuration in which a signal processing unit 23, a digital scan converter (DSC) 24, and an image processing unit 25 are serially connected. The signal processing unit 23 performs reception focus processing in which addition (phasing addition) is performed by giving each delay to each data of the received signals on the basis of a reception delay pattern selected depending on the control signal from the apparatus controller 16. Sound ray signals in which focal points of the ultrasonic echoes are narrowed to one scan line are generated by the reception focus processing. Additionally, the signal processing unit 23 performs correction of damping resulting from a propagated distance depending on the depth of a position where the ultrasonic waves have been reflected, on the generated sound ray signals, and then, performs envelope detection processing to generate B-mode image signals indicating a tissue within the subject. The B-mode image signals generated in this way are output to a DSC 24.

The DSC 24 of the image generation unit 5 raster-converts the B-mode image signals into image signals in accordance with a scan mode of normal television signals to generate an ultrasound image. The image processing unit 25 of the image generation unit 5 subjects the image data obtained in the DSC 24 to various kinds of required image processing, such as brightness correction, grayscale correction, sharpness correction, and color correction, and then outputs an ultrasound image to the display controller 6, the reference image holding unit 9, the movement vector calculation unit 10, and the tomographic plane determination unit 13.

Here, generally, a DVT is known as a disease in which a thrombus occurs in a deep vein. Although a normal deep vein in which the thrombus does not occur is easily deformed by compression, the deep vein in which the thrombus has occurred is not easily deformed due to the compression. Therefore, as a test for discovering the DVT, for example, a so-called compression test in which a cross-section of the compressed deep vein is observed while compressing the deep vein with a concern that the DVT may occur is performed. The cross-section of the deep vein represents the section of the deep vein in a case where cutting is performed so as to transverse a central axis of the deep vein. Additionally, usually, the compression test is performed by observing the acquired ultrasound image while pressing the ultrasound probe 19 against the body surface of the subject to compress observation targets, such as the deep vein.

Figure 4:
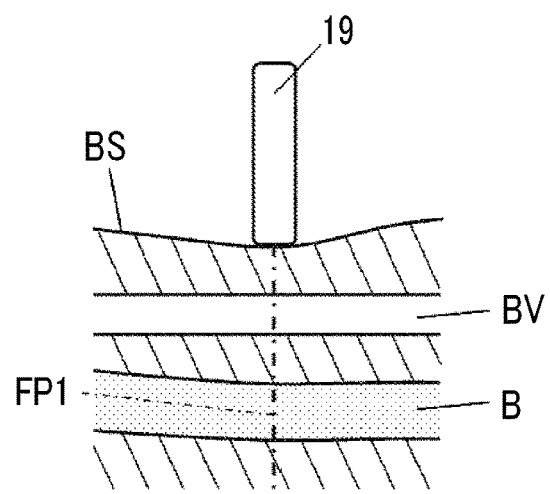
FIG. 4 is a schematic cross-sectional view of a subject in that an ultrasound probe is in contact with a body surface.

As illustrated in FIG. 4, the reference image holding unit 9 of the processor 20 stores the ultrasound image acquired by the image acquisition unit 8 as a reference image in a state where the position of the ultrasound probe 19 is fixed and the observation target is not yet compressed by the ultrasound probe 19 in order to depict a tomographic plane of an observation target, such as a blood vessel, on the display unit 7 in a case where the compression test is performed. In an example illustrated in FIG. 4, since the ultrasound probe 19 is in contact with a body surface BS of the subject but is not strongly pressed, tissue of the subject is not compressed, and a blood vessel BV, a bone B, and the like that are present in a subcutaneous part are in a state where deformation and movement accompanying the compression are not made. In this way, the reference image indicates, in the compression test, a tomographic plane FP1 of the subject in a state where the ultrasound probe 19 is positioned and the tissue of the subject is not compressed.

Here, although the deformation and movement of the tissue of the subject occur by the ultrasound probe 19 being pressed against the body surface BS of the subject in the compression test the movement vector calculation unit 10 of the processor 20 calculates the movement change of an ultrasound image in order to measure such deformation and movement of the tissue of the subject. More specifically, the movement vector calculation unit 10 calculates a movement vector indicating an image movement change between two consecutive ultrasound images for each frame among the ultrasound images sequentially acquired by the image acquisition unit 8. For example, the movement vector calculation unit 10 can calculate respective movement changes of respective pixels, that is, all pixels, in two consecutive ultrasound images, as movement vectors by performing image analysis, such as so-called matching processing, on the ultrasound images.

The movement vector integration unit 11 of the processor 20 integrates the movement vectors that are respectively calculated by the movement vector calculation unit 10 in the ultrasound images from the time when the reference image is stored by the reference image holding unit 9 until the current time, that is, from an ultrasound image stored as the reference image to an ultrasound image in the current frame. For example, in a case where the movement vector is calculated by the movement vector calculation unit 10 for each frame with respect to the ultrasound images of N frames from the time when the reference image is held by the reference image holding unit 9 until the current time, the movement vector integration unit 11 calculates an integration vector indicating how much a pixel within an ultrasound image have moved and changed as an integrated movement change from the ultrasound image held as the reference image to an ultrasound image of an N-th frame, that is, a current frame S. In this case, the movement vector integration unit 11 holds, for example, an integration vector indicating an integrated movement change from a first frame to an N−1th frame, and can calculate the integration vector from the first frame to the N-th frame by adding a movement vector indicating a movement change between the ultrasound image of the N−1th frame and the ultrasound image of the N-th frame, and the held integration vector.

The deformed image generation unit 12 of the processor 20, on the basis of the movement change integrated by the movement vector integration unit 11, generates a deformed image D1 obtained by moving and changing the ultrasound image stored as the reference image by the reference image holding unit 9 until the current time. For example, the deformed image generation unit 12 can generate the deformed image D1 by moving all the pixels of the ultrasound image stored as the reference image in accordance with the integrated movement change, respectively.

As illustrated in FIG. 1, the tomographic plane determination unit 13 of the processor 20 determines whether or not a tomographic plane of the subject depicted from the reference image and a tomographic plane of the subject depicted from the ultrasound image of the current frame are the same as each other by comparing the deformed image D1 generated by the deformed image generation unit 12 with an ultrasound image C1 of the current frame acquired by the image acquisition unit 8. In this case, by performing image analysis on the deformed image D1 and the ultrasound image C1 of the current frame, the tomographic plane determination unit 13 calculates similarity between these two images, and performs determination on the basis of the calculated similarity. For example, the tomographic plane determination unit 13 can determine that the tomographic plane of the subject depicted from the reference image and the tomographic plane of the subject depicted from the ultrasound image C1 of the current frame are the same as each other in a case where the calculated similarity is equal to or more than a threshold, and can determine that the tomographic plane of the subject depicted from the reference image and the tomographic plane of the subject depicted from the ultrasound image C1 of the current frame are different from each other in a case where the calculated similarity is smaller than the threshold.

Figure 5:
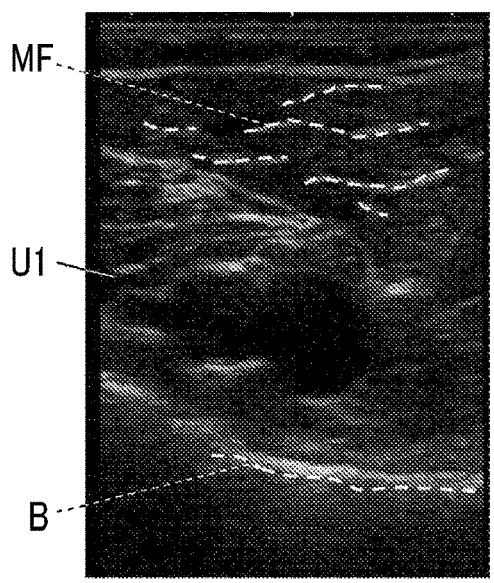
FIG. 5 is an ultrasound image illustrating a tomographic plane of the subject in a state of not being pressed by an ultrasound probe.
Figure 6:
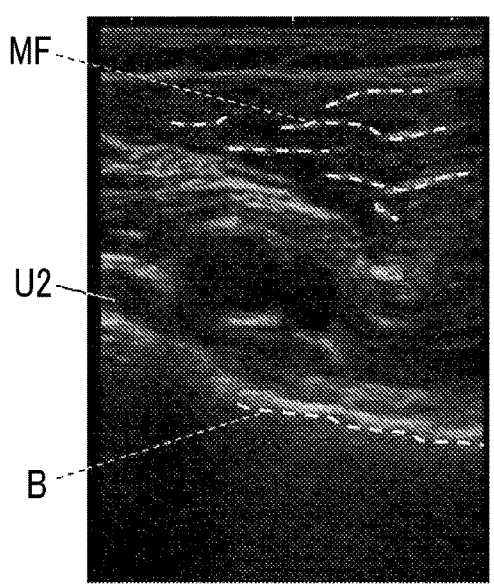
FIG. 6 is an ultrasound image illustrating the tomographic plane of the subject in a state of being pressed by the ultrasound probe.

Here, in a case where the tomographic plane FP1 of the subject depicted from the ultrasound image C1 of the current frame is the same as the tomographic plane FP1 of the subject depicted from the reference image, for example, as illustrated in FIGS. 5 and 6, a difference between the ultrasound image C1 of the current frame and the reference image greatly originates in the image movement change caused by the ultrasound probe 19 being pressed against the body surface BS of the subject. For that reason, in this case, the similarity between the ultrasound image C1 of the current frame and the deformed image D1 becomes high. Here, FIG. 5 illustrates an ultrasound image U1 in which the tissue of the subject corresponding to the reference image is not compressed by the ultrasound probe 19, FIG. 6 illustrates an ultrasound image U2 in which the tissue of the subject is compressed by the ultrasound probe 19, and a tomographic plane of the subject depicted from the ultrasound image U1 and a tomographic plane of the subject depicted from the ultrasound image U2 are the same as each other. Comparing FIG. 5 with FIG. 6, it can be seen that, as the tissue of the subject is compressed by the ultrasound probe 19, muscle-fibers MF are deformed and the bone B moves above the image.

Figure 7:
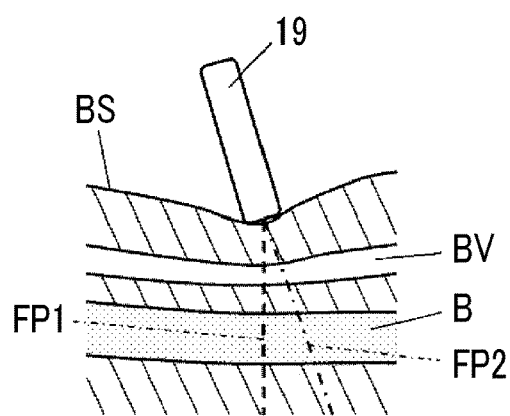
FIG. 7 is a schematic cross-sectional view of the subject pressed by the ultrasound probe.
Figure 8:
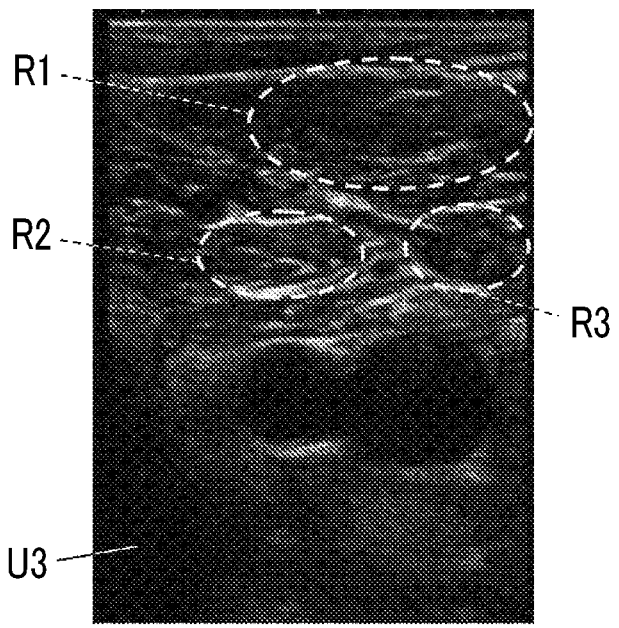
FIG. 8 is an ultrasound image illustrating a tomographic plane of the subject depicted from a reference image.
Figure 9:
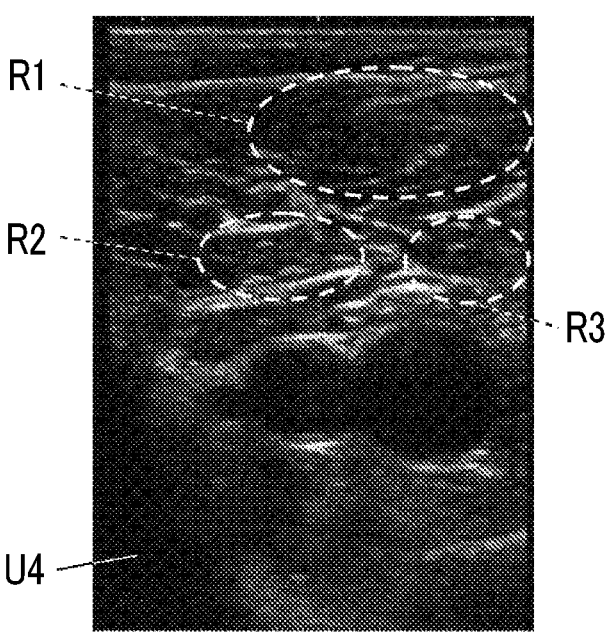
FIG. 9 is an ultrasound image illustrating a tomographic plane different from the tomographic plane of the subject depicted from the reference image.

On the other hand, as illustrated in FIG. 7, in a case where the ultrasound probe 19 inclines in a case where the ultrasound probe 19 is pressed against the body surface BS of the subject, and the tomographic plane FP2 of the subject depicted from the ultrasound image C1 of the current frame is greatly different from the tomographic plane FP1 of the subject depicted from the reference image, for example, as illustrated in FIGS. 8 and 9, the difference between the ultrasound image C1 of the current frame and the reference image cannot be indicated only by a movement change of a simple image. For that reason, in this case, the similarity between the ultrasound image C1 of the current frame and the deformed image D1 becomes low. Here, FIG. 8 illustrates an ultrasound image U3 by which the same tomographic plane as the tomographic plane FP1 of the subject depicted from the reference image is depicted, and FIG. 9 illustrates an ultrasound image U4 by which the tomographic plane FP2 inclined from the tomographic plane FP1 is depicted. Additionally, as illustrated in FIGS. 8 and 9, structure patterns of muscle fibers indicated by pixels with high luminance are included within regions R1, R2, and R3 that are respectively surrounded by broken lines in the ultrasound image U3 and the ultrasound image U4. It can be seen that the structure patterns of the muscle fibers within the regions R1, R2, and R3 in the ultrasound image U3 are different from the structure patterns of the muscle fibers within the regions R1, R2, and R3 in the ultrasound image U4, and cannot be indicated by a movement change of a simple image.

In this way, it can be seen that it can be determined whether or not the tomographic plane of the subject depicted from the ultrasound image C1 of the current frame and the tomographic plane of the subject depicted from the reference image are the same as each other on the basis of the similarity between the deformed image D1 and the ultrasound image C1 of the current frame.

Additionally, the tomographic plane determination unit 13 calculates the similarity between the deformed image D1 and the ultrasound image C1 of the current frame by performing the image analysis on the deformed image D1 and the ultrasound image C1 of the current frame. However, more specifically, for example, the tomographic plane determination unit 13 can perform so-called matching between frames on the deformed image D1 and the ultrasound image C1 of the current frame to calculate the similarity. Additionally, for example, a machine learning technique described in Csurka et al.: Visual Categorization with Bags of Keypoints, Proc. of ECCV Workshop on Statistical Learning in Computer Vision, pp. 59-74 (2004), a general image recognition technique using deep learning described in Krizhevsky et al.: Image Net Classification with Deep Convolutional Neural Networks, Advances in Neural Information Processing Systems 25, and pp. 1106-1114 (2012), or the like in addition to the simple matching can be used for the calculation of the similarity.

The determination result notification unit 14 of the processor 20 notifies a user of a determination result caused by the tomographic plane determination unit 13. Although not illustrated, the determination result notification unit 14 can notify the user of the determination result, for example, by displaying, on the display unit 7, texts, images, or the like indicating that the tomographic plane of the subject depicted from the ultrasound image C1 of the current frame is the same as or different from the tomographic plane of the subject depicted from the reference image, as the determination result. Additionally, although not illustrated, for example, a voice generation unit that generates voice may also be provided in the ultrasound diagnostic apparatus 1, and the determination result notification unit 14 can also notify the user of the determination result via the voice caused by the voice generation unit.

In this way, since the user is notified of the determination result automatically obtained by the tomographic plane determination unit 13 by the determination result notification unit 14, the user can grasp easily whether or not tomographic plane of the subject depicted currently is a tomographic plane that the user has intended.

The trigger signal transmitting unit 15 of the processor 20 transmits trigger signal indicating that operation is newly started with respect to the reference image holding unit 9 and the movement vector integration unit 11 by the operation of the user via the input unit 17. Here, in a case where the reference image holding unit 9 has received the trigger signal from the trigger signal transmitting unit 15, the reference image holding unit 9 writes an ultrasound image newly acquired by the image acquisition unit 8 over the ultrasound image already held as the reference image, and holds the overwritten ultrasound image as a new reference image. Additionally, in a case where the movement vector integration unit 11 has received the trigger signal, the movement vector integration unit 11 eliminates the image movement change that has already been integrated, and starts integration of a movement vector newly calculated by the movement vector calculation unit 10.

The apparatus controller 16 of the processor 20 performs control of the respective units of the ultrasound diagnostic apparatus 1 on the basis of the programs that are stored in advance by the storage unit 18 and the like and the operation of the user via the input unit 17.

The display controller 6 of the processor 20 performs predetermined processing under the control of the apparatus controller 16 on an ultrasound image generated by the image generation unit 5 of the image acquisition unit 8, and displays the ultrasound image on the display unit 7.

The display unit 7 of the ultrasound diagnostic apparatus 1 displays an ultrasound image and the like under the control of the display controller 6, and includes, for example, display units, such as a liquid crystal display (LCD) and an organic electroluminescence display (EL).

The input unit 17 of the ultrasound diagnostic apparatus 1 is for the user to perform input operation, and can be configured to comprise a keyboard, a mouse, a trackball, a touchpad, a touch panel, and the like.

The storage unit 18 stores operating programs and the like of the ultrasound diagnostic apparatus 1, and memory media, such as a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), a universal serial bus memory (USB memory), servers, or the like can be used.

In addition, although the processor 20 having the display controller 6, the image acquisition unit 8, the reference image holding unit 9, the movement vector calculation unit 10, the movement vector integration unit 11, the deformed image generation unit 12, the tomographic plane determination unit 13, the determination result notification unit 14, the trigger signal transmitting unit 15, and the apparatus controller 16 the processor 20 may be configured from a central processing unit (CPU) and control programs for making the CPU perform various kinds of processing, may be configured using a field programmable gate array (FPGA), a digital signal processor (DSP), an application specific integrated circuit (ASIC), other integrated circuits (ICs), or may be configured by combining them.

Additionally, the display controller 6, the image acquisition unit 8, the reference image holding unit 9, the movement vector calculation unit 10, the movement vector integration unit 11, the deformed image generation unit 12, the tomographic plane determination unit 13, the determination result notification unit 14, the trigger signal transmitting unit 15, and the apparatus controller 16 of the processor 20 can also be configured to be partially or entirely integrated into one CPU.

Figure 10:
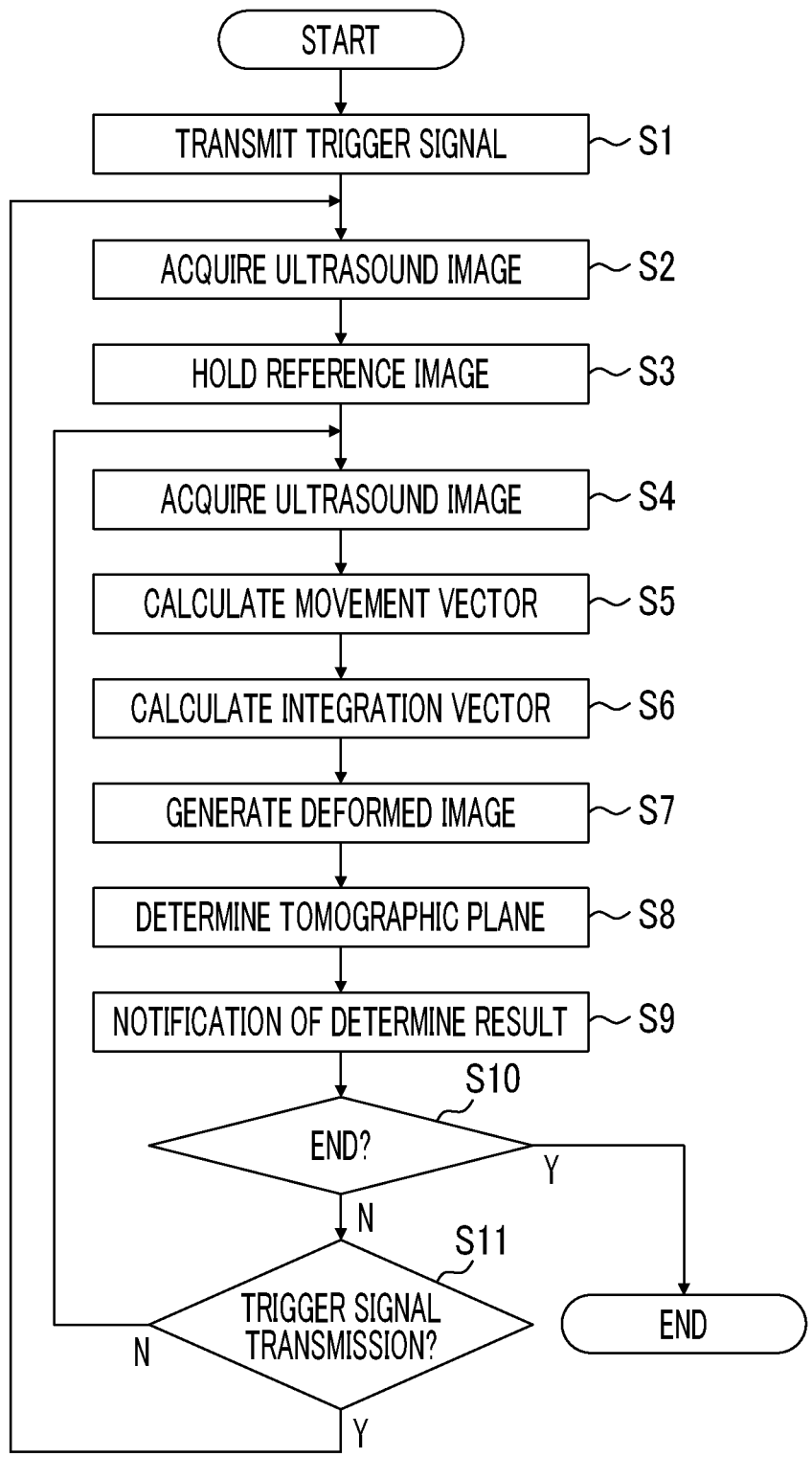
FIG. 10 is a flowchart illustrating the operation of the ultrasound diagnostic apparatus related to Embodiment 1 of the invention.

Next, the operation of the ultrasound diagnostic apparatus 1 in Embodiment 1 will be described in detail, using a flowchart illustrated in FIG. 10. The flowchart illustrated in FIG. 10 illustrates the operation of the ultrasound diagnostic apparatus 1 in a case where a compression test of a subject is performed.

First, in Step S1, a user fixes the position of the ultrasound probe 19 in order to depict a tomographic plane of an observation target, such as the blood vessel BV, for example, as illustrated in FIG. 4. Moreover, in a case where information indicating that a trigger signal is to be transmitted is input by the user via the input unit 17, the trigger signal transmitting unit 15 transmits the trigger signal to the reference image holding unit 9 and the movement vector integration unit 11.

Next, in Step S2, an ultrasound beam is transmitted toward the subject from the oscillator array 2 of the ultrasound probe 19, and received signals are generated by the oscillator array 2 on the basis of ultrasonic echoes propagated toward the oscillator array 2 from the subject. Thus, as the received signals generated in this way are sequentially processed by the receiving unit 4 and the image generation unit 5 of the image acquisition unit 8, an ultrasound image representing a tomographic plane of the subject is acquired.

In Step S3, the reference image holding unit 9 holds the ultrasound image acquired in Step S2 as a reference image.

In Step S4, the image acquisition unit 8 acquires an ultrasound image similarly to Step S2.

In Step S5, the movement vector calculation unit 10 calculates a movement vector indicating an image movement change between two consecutive ultrasound images, that is, the two ultrasound images acquired in Step S2 and Step S4. Hereinafter, it is assumed that the movement vector calculation unit 10 calculates movement changes of all pixels in the two ultrasound images as the movement vectors, respectively, for description.

In Step S6, the movement vector integration unit 11 integrates the movement vector calculated in Step S5. The movement vector integration unit 11 performs, for example, integration of the movement vectors for each of all the pixels of the ultrasound images. At the current time, since the movement vector calculated in Step S5 is only one per each pixel, an integration result, that is, an integration vector, obtained in Step S6 is equal to the movement vector calculated in Step S5. Additionally, the movement vector integration unit 11 holds the newest integration vector obtained in Step S6.

In Step S7, the deformed image generation unit 12 generates a deformed image D1 obtained by moving and changing of the ultrasound image held as the reference image in Step S3 until the current time, that is, until the ultrasound image is acquired in Step S4, on the basis of a movement change of the integrated image in Step S6. The deformed image generation unit 12 generates the deformed image D1, for example, by moving all the pixels of the reference image in accordance with the movement change integrated in Step S6.

In Step S8, the tomographic plane determination unit 13 determines whether or not the tomographic plane of the subject depicted from the reference image and the tomographic plane of the subject depicted from the ultrasound image C1 of the current frame are the same as each other by comparing the deformed image D1 generated in Step S7 with the ultrasound image C1 of the current frame acquired in Step S4. The tomographic plane determination unit 13 can calculate the similarity between the deformed image D1 and the ultrasound image C1 of the current frame, for example, by performing matching between frames on the deformed image D1 and the ultrasound image C1 of the current frame, and can perform determination on the basis of the calculated similarity.

In Step S9, the determination result notification unit 14 notifies the user of a determination result obtained in Step S8. For example, the determination result notification unit 14 can notify the user of the determination result by superimposing and displaying texts, images, or the like indicating the determination result on the ultrasound image C1 of the current frame.

In Step S10, whether or not to end the operation of the ultrasound diagnostic apparatus 1 is determined. For example, although not illustrated, it is determined that the operation of the ultrasound diagnostic apparatus 1 is ended in a case where an end button for ending the operation of the ultrasound diagnostic apparatus 1 is displayed on the display unit 7, and the end button is pushed by the user via the input unit 17, and it is determined that the operation of the ultrasound diagnostic apparatus 1 is not ended in a case where the end button is not pushed. In Step S10, in a case where it is determined that the operation of the ultrasound diagnostic apparatus 1 is not ended, the process proceeds to Step S11.

In the following Step S11, whether or not a trigger signal has been newly transmitted by the trigger signal transmitting unit 15 is determined. In this case, in a case where the information indicating that a trigger signal is to be transmitted is not newly input by the user via the input unit 17 and a trigger signal is not newly transmitted by the trigger signal transmitting unit 15, it is determined that the trigger signal is not newly transmitted, and the process returns to Step S4.

In Step S4, an ultrasound image is newly acquired by the image acquisition unit 8.

In the following Step S5, the movement vector calculation unit 10 calculates a movement vector on the basis of the two ultrasound images acquired in the current Step S4 and the previous Step S4.

In Step S6, the movement vector integration unit 11 calculates an integrated movement change from the time when the reference image is held in Step S3 until the current time. In this case, the movement vector integration unit 11 calculates a new integration vector by adding the newest integration vector that is held to the movement vector newly obtained in Step S5. Since the newest integration vector held at the current time is equal to a movement vector calculated from an ultrasound image of a first frame and an ultrasound image of a second frame, the movement vector integration unit 11 adds the movement vector calculated from the ultrasound image of the first frame and the ultrasound image of the second frame to the movement vector newly obtained in Step S5, in all the pixels of the ultrasound images. Additionally, the movement vector integration unit 11 holds the new integration vector calculated in Step S6 instead of the integration vector already held.

In Step S7, the deformed image generation unit 12 deforms the ultrasound image indicating the reference image held in Step S3 to newly generate a deformed image D1 on the basis of the movement change of each pixel newly integrated in Step S6.

In Step S8, the tomographic plane determination unit 13 determines whether or not the tomographic plane of the subject depicted from the ultrasound image held as the reference image and the tomographic plane of the subject depicted from the ultrasound image C1 of the current frame are the same as each other by comparing the deformed image D1 newly generated in Step S7 with the ultrasound image C1 of the current frame newly acquired in Step S4.

In Step S9, the determination result notification unit 14 notifies the user of a determination result newly obtained in Step S8.

In the following Step S10, determines whether or not the operation of the ultrasound diagnostic apparatus 1 is ended. In Step S10, in a case where it is determined that the operation of the ultrasound diagnostic apparatus 1 is not ended, the process proceeds to Step S11.

In Step S11, determines whether or not a trigger signal has been newly transmitted by the trigger signal transmitting unit 15.

In this way, the processing of Step S4 to Step S11 is repeated until it is determined that the operation of the ultrasound diagnostic apparatus 1 is ended in Step S10 or determines that the trigger signal has been newly transmitted by the trigger signal transmitting unit 15 in Step S11. In this case, in Step S6, the movement vector integration unit 11 calculates a new integration vector by adding the held newest integration vector to the movement vector newly calculated in Step S5. Moreover, the movement vector integration unit 11 holds the newly calculated integration vector instead of the integration vector held until now. Whenever Step S4 to Step S11 are repeated in this way, the new deformed image D1 is generated in Step S7, and the determination of Step S8 is performed on the basis of the generated new deformed image D1 and the ultrasound image C1 of the current frame, and the user is notified of the determination result in Step S9.

Additionally, in Step S11, in a case where the information indicating that a trigger signal is to be transmitted is newly input by the user via the input unit 17 and the trigger signal is transmitted by the trigger signal transmitting unit 15, it is determined that the trigger signal has been newly transmitted, and the process returns to Step S2. In this case, the position of the ultrasound probe 19 is fixed in a state where the user does not compress the subject by the ultrasound probe 19, for example, as illustrated in FIG. 4. In this way, in a case where the trigger signal is newly transmitted to the reference image holding unit 9 and the movement vector integration unit 11 by the trigger signal transmitting unit 15, the reference image holding unit 9 eliminates the reference image held until now, and the movement vector integration unit 11 eliminates the held integration vector.

In Step S2, the image acquisition unit 8 newly acquires an ultrasound image.

In the following Step S3, the reference image holding unit 9 holds the ultrasound image newly acquired in Step S2 as a reference image.

In Step S4, the image acquisition unit 8 newly acquires an ultrasound image similarly to Step S2.

In Step S5, the movement vector calculation unit 10 calculates a movement vector indicating an image movement change between the two ultrasound images acquired in Step S2 and Step S4.

In Step S6, the movement vector integration unit 11 integrates the movement vector calculated in Step S5. Here, since the trigger signal is transmitted to the movement vector integration unit 11 by the trigger signal transmitting unit 15 in Step S11, the integration vector held by the movement vector integration unit 11 is eliminated. For that reason, the current integration vector caused by the movement vector integration unit 11 is equal to the movement vector calculated in Step S5.

In Step S7, the deformed image generation unit 12 generates a deformed image D1 by deforming the ultrasound image newly held as the reference image by Step S3 on the basis of the integrated movement change in Step S6.

In Step S8, the tomographic plane determination unit 13 determines whether or not a tomographic plane of the subject depicted from the reference image newly held in Step S3 and a tomographic plane of the subject depicted from the ultrasound image C1 of the current frame are the same as each other by comparing the deformed image D1 generated in Step S7 with the ultrasound image C1 of the current frame acquired in Step S4.

In Step S9, the determination result notification unit 14 notifies the user of a determination result obtained in Step S8.

In the following Step S10, whether or not to end the operation of the ultrasound diagnostic apparatus 1 is determined. In Step S10, in a case where it is determined that the operation of the ultrasound diagnostic apparatus 1 is not ended, the process proceeds to Step S11. Additionally, in Step S10 in a case where it is determined that the operation of the ultrasound diagnostic apparatus 1 is determined, the operation of the ultrasound diagnostic apparatus 1 is ended.

From above, according to the ultrasound diagnostic apparatus 1 related to Embodiment 1 of the invention, the deformed image D1 obtained by deforming the ultrasound image held as the reference image is generated by the deformed image generation unit 12 on the basis of the integrated movement change from the time when the reference image is held by the reference image holding unit 9 until the current time, the deformed image D1 and the ultrasound image C1 of the current frame are compared with each other by the tomographic plane determination unit 13 to determine the tomographic planes, and the user is notified of the determination result by the determination result notification unit 14. Therefore, the user can easily grasp whether or not the tomographic plane of the subject currently depicted on the display unit 7 is an intended tomographic plane, and can perform an accurate diagnosis.

In addition, in Embodiment 1, a case in which it is determined that the tomographic plane of the subject depicted from the reference image and the tomographic plane of the subject depicted from the ultrasound image C1 of the current frame are the same as each other in a case where the similarity between the deformed image D1 and the ultrasound image C1 of the current frame is equal to or more than the threshold by the tomographic plane determination unit 13, and it is determined that the tomographic plane of the subject depicted from the reference image and the tomographic plane of the subject depicted from the ultrasound image C1 of the current frame are different from each other in a case where the similarity is smaller than the threshold is described. However, the determination method of the tomographic plane determination unit 13 is not particularly limited to this.

For example, the tomographic plane determination unit 13 can also divide the criteria for the determination of the similarity into a plurality of level, and determine the tomographic planes depending which level the calculated similarity belongs to. For example, the tomographic plane determination unit 13 can determine that the two tomographic planes of the tomographic plane of the subject depicted from the reference image and the tomographic plane of the subject depicted from the ultrasound image C1 of the current frame are the same as each other in a case where the calculated similarity is equal to or more than a first threshold, determine that there is high possibility that the two tomographic planes are the same as each other in a case where the calculated similarity is smaller than the first threshold and equal to more than a second threshold, and determine that the two tomographic planes are different from each other in a case where the calculated similarity is smaller than the second threshold.

In this case, for example, the determination result notification unit 14 can superimpose and display texts, images, or the like indicating the determination result according to the levels of determination caused by the tomographic plane determination unit 13 on the ultrasound image C1 of the current frame. Additionally, for example, the determination result notification unit 14 can also apply colors according to the levels of similarity to the ultrasound image C1 of the current frame to display the colors on the display unit 7. Additionally, the determination result notification unit 14 can also superimpose and display the value of the similarity calculated by the tomographic plane determination unit 13 on the ultrasound image C1 of the current frame.

In this way, since the tomographic planes are determined depending on the levels of similarity by the tomographic plane determination unit 13 and the user is notified of the determination result by the determination result notification unit 14, the user can perform more accurate diagnosis by checking the determination result.

Additionally, although not illustrated, in a case where the deformed image generation unit 12 is connected to the display controller 6, the deformed image generation unit 12 can display the deformed image D1 along with the ultrasound image C1 of the current frame on the display unit 7. Accordingly, the user can visually and directly compare the ultrasound image C1 with the deformed image D1 of the current frame, and can more accurately determine whether or not the tomographic plane of the subject depicted from the ultrasound image C1 of the current frame and the tomographic plane of the subject depicted from the reference image are the same as each other.

Additionally, the movement vector calculation unit 10 can interpolate the movement vector of each pixel in an ultrasound image, using a plurality of calculated movement vectors. More specifically, for example, the movement vector calculation unit 10 can interpolate the movement vector of each pixel by calculating movement vectors by image analysis with respect to all the pixels in the ultrasound image, weight-averaging a plurality of movement vectors calculated for each pixel and pixels located therearound, or the like. Accordingly, the movement vector calculation unit 10 can calculate a more accurate movement vector.

Additionally, in this case, since the movement vector integration unit 11 calculates the integration vector using the movement vector interpolated by the movement vector calculation unit 10, a more accurate integration vector can be calculated.

Additionally, in Embodiment 1, although the movement vector calculation unit 10 calculates the movement vectors with respect to all the pixels of an ultrasound image, respectively, the calculation method of the movement vectors is not particularly limited to this. For example, the movement vector calculation unit 10 can calculate a movement change of a high-luminance pixel of which the luminance is equal to or more than a predetermined threshold, among all the pixels of the ultrasound image, as a movement vector. In this case, the movement vector integration unit 11 integrates a movement vector for each high-luminance pixel of the ultrasound image, and the deformed image generation unit 12 generates the deformed image D1 on the basis of the movement change of each high-luminance pixel in the reference image.

Accordingly, since the number of pixels to be handled by the movement vector calculation unit 10, the movement vector integration unit 11, and the deformed image generation unit 12 can be reduced, the calculation load in the ultrasound diagnostic apparatus 1 can be mitigated.

Additionally, in this case, the deformed image generation unit 12 can generate the deformed image D1 by dividing an ultrasound image into a plurality of regions each including at least one high-luminance pixel, and by moving the plurality of regions, respectively, on the basis of the movement change integrated for each of the high-luminance pixels by the movement vector integration unit 11. Additionally, the tomographic plane determination unit 13 can perform determination of the tomographic planes for every multiple regions divided by the deformed image generation unit 12, and the determination result notification unit 14 can notify the user of determination result for every multiple regions.

Accordingly, since the determination result notification unit 14 can notify the user of a more detailed determination result, the user can more accurately perform whether or not the tomographic plane of the subject depicted from the ultrasound image C1 of the current frame and the tomographic plane of the subject depicted from the reference image are the same as each other.

Additionally, the movement vector calculation unit 10 can also perform the image analysis with respect to an ultrasound image to calculate the edge likeness of the image, and calculate a movement vector with respect to a pixel in which the calculated edge likeness is equal to or more than a threshold. Here, the edge likeness of the image is an index indicating profile-likeness on the image, and is calculated using the contrast or the like between target pixels and surrounding pixels.

Additionally, for example, the movement vector calculation unit 10 can also partition an ultrasound image into a predetermined number of regions, and calculate a movement change of one pixel in each region as a movement vector of each region. In this case, the movement vector integration unit 11 can integrate movement vectors for each of the regions partitioned by the movement vector calculation unit, and the deformed image generation unit 12 can generate the deformed image D1 on the basis of movement change of each region in the reference image.

Additionally, in this case, the tomographic plane determination unit 13 can calculate the similarity between the deformed image D1 and the ultrasound image C1 of the current frame for each of the regions partitioned by the movement vector calculation unit 10, and perform determination of the tomographic planes for each partitioned region on the basis of the calculated similarity. Moreover, the determination result notification unit 14 can notify the user of a determination result for every multiple partitioned regions.

Additionally, in Embodiment 1, the movement vector calculation unit 10 calculates a movement vector whenever an ultrasound image is sequentially and consecutively acquired by the image acquisition unit 8. However, a movement vector between two ultrasound images that are consecutive for every multiple predetermined frames can be calculated. Accordingly, since the number of movement vectors to be calculated by unit time by the movement vector calculation unit 10 can be reduced, the calculation load of the ultrasound diagnostic apparatus 1 can be mitigated.

Additionally, in Embodiment 1, the deformed image generation unit 12 generates the deformed image D1 immediately after a first integration vector is obtained by the movement vector integration unit 11. However, deformation and movement of the tissue of the subject are more reflected in the integration vector calculated by the movement vector integration unit 11 as the time during which the tissue of the subject is compressed by the ultrasound probe 19 elapses. Therefore, for example, generation of the deformed image D1 can be started from the time during which a movement vector is integrated with respect to ultrasound images of a given number of frames of five frames to ten frames.

Embodiment 2

Figure 11:
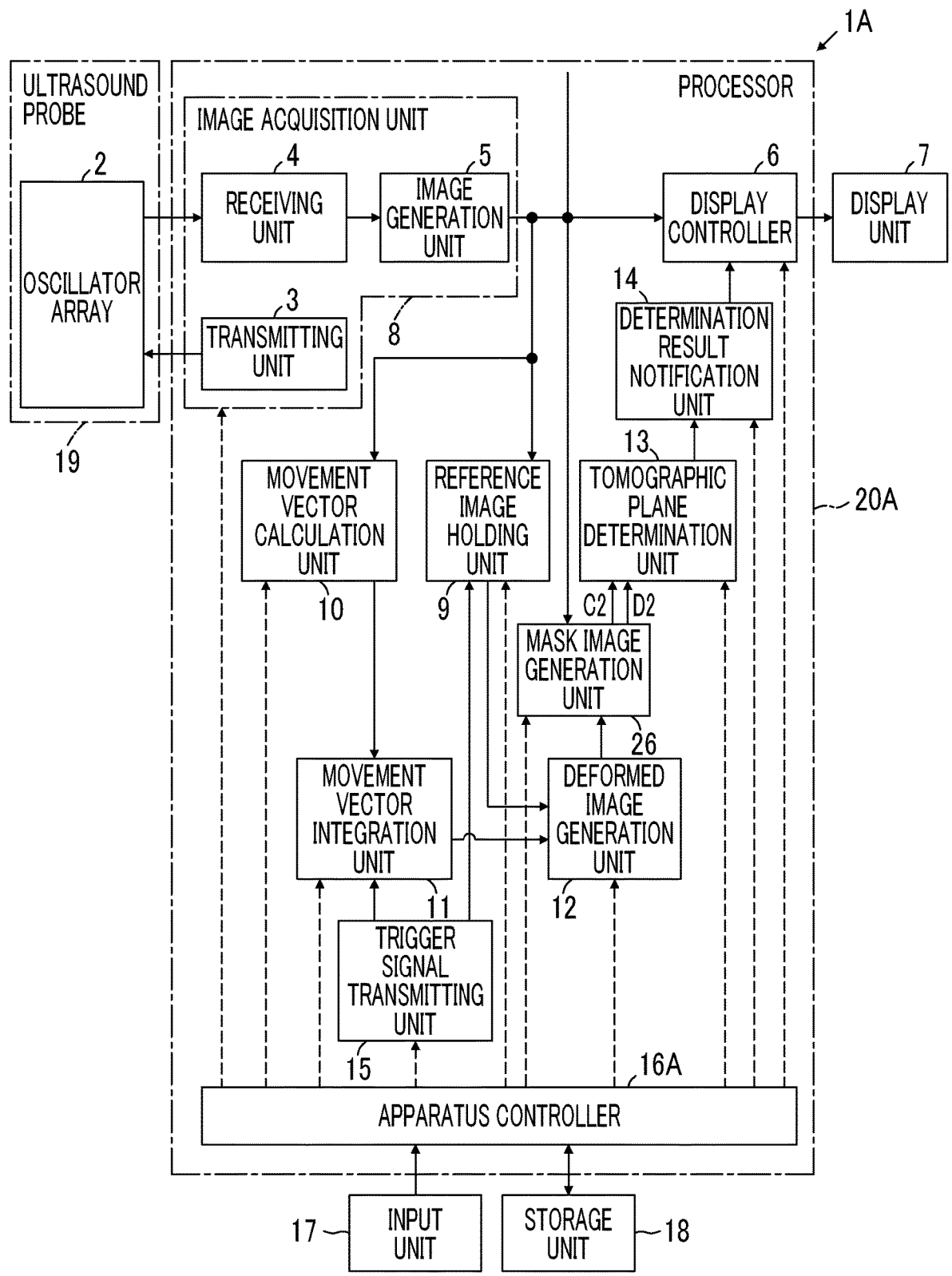
FIG. 11 is a block diagram illustrating the configuration of an ultrasound diagnostic apparatus related to Embodiment 2 of the invention.

The configuration of an ultrasound diagnostic apparatus 1A related to Embodiment 2 is illustrated in FIG. 11. The ultrasound diagnostic apparatus 1A of Embodiment 2 comprises an apparatus controller 16A instead of the apparatus controller 16 in the ultrasound diagnostic apparatus 1 of Embodiment 1 illustrated in FIG. 1, and an added mask image generation unit 26.

In the ultrasound diagnostic apparatus 1A of Embodiment 2, the mask image generation unit 26 is connected to the image generation unit 5 and the deformed image generation unit 12, and the tomographic plane determination unit 13 is connected to the mask image generation unit 26. Additionally, the apparatus controller 16A is connected to the display controller 6, the image acquisition unit 8, the reference image holding unit 9, the movement vector calculation unit 10, the movement vector integration unit 11, the deformed image generation unit 12, the tomographic plane determination unit 13, the determination result notification unit 14, the trigger signal transmitting unit 15, and the mask image generation unit 26. Additionally, the input unit 17 and the storage unit 18 are connected to the apparatus controller 16A. Here, the apparatus controller 16A and the storage unit 18 are connected to each other so as to be capable of transferring information bidirectionally.

Moreover, a processor 20A is configured by the display controller 6, the image acquisition unit 8, the reference image holding unit 9, the movement vector calculation unit 10, the movement vector integration unit 11, the deformed image generation unit 12, the tomographic plane determination unit 13, the determination result notification unit 14, the trigger signal transmitting unit 15, the apparatus controller 16A and the mask image generation unit 26.

Here, in a case where a test of the DVT is performed, a blood vessel, a muscle fiber, a bone, a nerve, a tendon, and the like are often included within an ultrasound image. However, for example, as illustrated in FIG. 7, in a case where a tomographic plane depicted from the ultrasound image as the ultrasound probe 19 is inclined has changed from the tomographic plane FP1 to the tomographic plane FP2, a change in a structure pattern of the muscle fibers and the bone expressed by pixels with high luminance in the ultrasound image is particularly remarkable. Regarding the muscle fibers, as illustrated in FIGS. 8 and 9, it can be seen that, as a tomographic plane depicted from the ultrasound image shifts, structure patterns of the muscle fibers in regions R1, R2, and R3 change. Additionally, although the bone is not illustrated, the structure of a section change depending on a spot, and the shape of the surface of the bone is not uniform. Therefore, in a case where the tomographic plane depicted from the ultrasound image shifts, the structure pattern of the bone changes. For that reason, determination of tomographic planes is more easily performed by comparing a deformed image with an ultrasound image of a current frame while paying attention to at least one of the muscle fibers or the bone.

The mask image generation unit 26 of the processor 20A performs image analysis on an ultrasound image of the current frame acquired by the image acquisition unit 8 and a deformed image generated by the deformed image generation unit 12, respectively, to detect at least one of muscle fibers or a bone, and generates a mask image C2 in which regions other than the muscle fibers and the bone detected with respect to the ultrasound image of the current frame are masked, and a mask image D2 in which the regions other than the muscle fibers and the bone detected with respect to the deformed image are masked. Here, masking the regions other than the muscle fibers and the bone means covering regions other than the muscle fibers and the bone within an ultrasound image, and includes superimposing and painting away or shading, an image for covering a target region, or the like. Additionally, in a case where the regions other than the muscle fibers and the bone, it can be seen that, as long as the target region is covered, for example, an image having transmittance, such as a translucent image may be superimposed.

Here, generally, since the signal intensity of ultrasonic echoes from the surface of a bone is stronger than the signal intensity of the ultrasonic echoes from other than the bone, the mask image generation unit 26 can detect, for example, a region where the luminance within an ultrasound image is equal to or more than the threshold, as a region indicating the bone. Additionally, the mask image generation unit 26 can detect, for example, a blood vessel, a bone, a nerve, a tendon, and the like, and then the remaining region as a region indicating muscle fibers.

Generally, since the cross-section of a blood vessel and the cross-section of a nerve bundle are observed as approximately circular regions, the mask image generation unit 26 can detect the blood vessel and the nerve bundle, for example, using Hessian-matrix H of the following Expression (1).

$$H = \begin{bmatrix} L_{xx} & L_{xy} \\ L_{xy} & L_{yy} \end{bmatrix} \quad (1)$$

Here, with $G(\sigma)$ being Gaussian filter with a standard deviation $\sigma$ and I being an input image, and $L_{xx}$, $L_{xy}$, and $L_{yy}$ are expressed by the following Expressions (2), (3), and (4), respectively.

$$L_{xx} = \frac{\partial^2}{\partial x^2} G(\sigma) * I \quad (2)$$

$$L_{xy} = \frac{\partial^2}{\partial x \partial y} G(\sigma) * I \quad (3)$$

$$L_{yy} = \frac{\partial^2}{\partial y^2} G(\sigma) * I \quad (4)$$

Generally, the more the regions having isotropic shape, the more a determinant, that is, $L_{xx} \cdot L_{yy} - (L_{xy})^2$ of the Hessian-matrix H, which are expressed by the formula (1), has a positive large value. Therefore, the mask image generation unit 26 can detect, for example, a region where the determinant of the Hessian-matrix H is equal to or more than a predetermined positive threshold as a region indicating the blood vessel or the nerve bundle.

Additionally, usually, a tendon is often observed as a structure of which the luminance is high in a deep part of an ultrasound image. Therefore the mask image generation unit 26 can detect, for example, a region that is shallower than the predetermined depth in the ultrasound image and has a luminance equal to or more than the threshold, as a region indicating the tendon.

As illustrated in FIG. 11, the tomographic plane determination unit 13 of the processor 20A determines whether or not the tomographic plane of the subject depicted from the reference image and the tomographic plane of the subject depicted from the ultrasound image of the current frame are the same as each other by comparing the mask image C2 for the ultrasound image of the current frame with the mask image D2 for the deformed image, which are generated by the mask image generation unit 26.

In this case, the tomographic plane determination unit 13 can calculate, for example, the similarity between mask image C2 for the ultrasound image of the current frame and the mask image D2 for the deformed image, can determine that the tomographic plane of the subject depicted from the reference image and the tomographic plane of the subject depicted from the ultrasound image of the current frame are the same as each other in a case where the calculated similarity is equal to or more than a threshold, and can determine that the tomographic plane of the subject depicted from the reference image and the tomographic plane of the subject depicted from the ultrasound image of the current frame are different from each other in a case where the similarity is smaller than the threshold.

In this way, since the ultrasound image of the current frame and the deformed image can be compared with each other while paying attention to at least one of the muscle fibers or the bone by comparing the mask image C2 for the ultrasound image of the current frame with the mask image D2 for the deformed image, determination of the tomographic planes is more easily and accurately performed.

Figure 12:
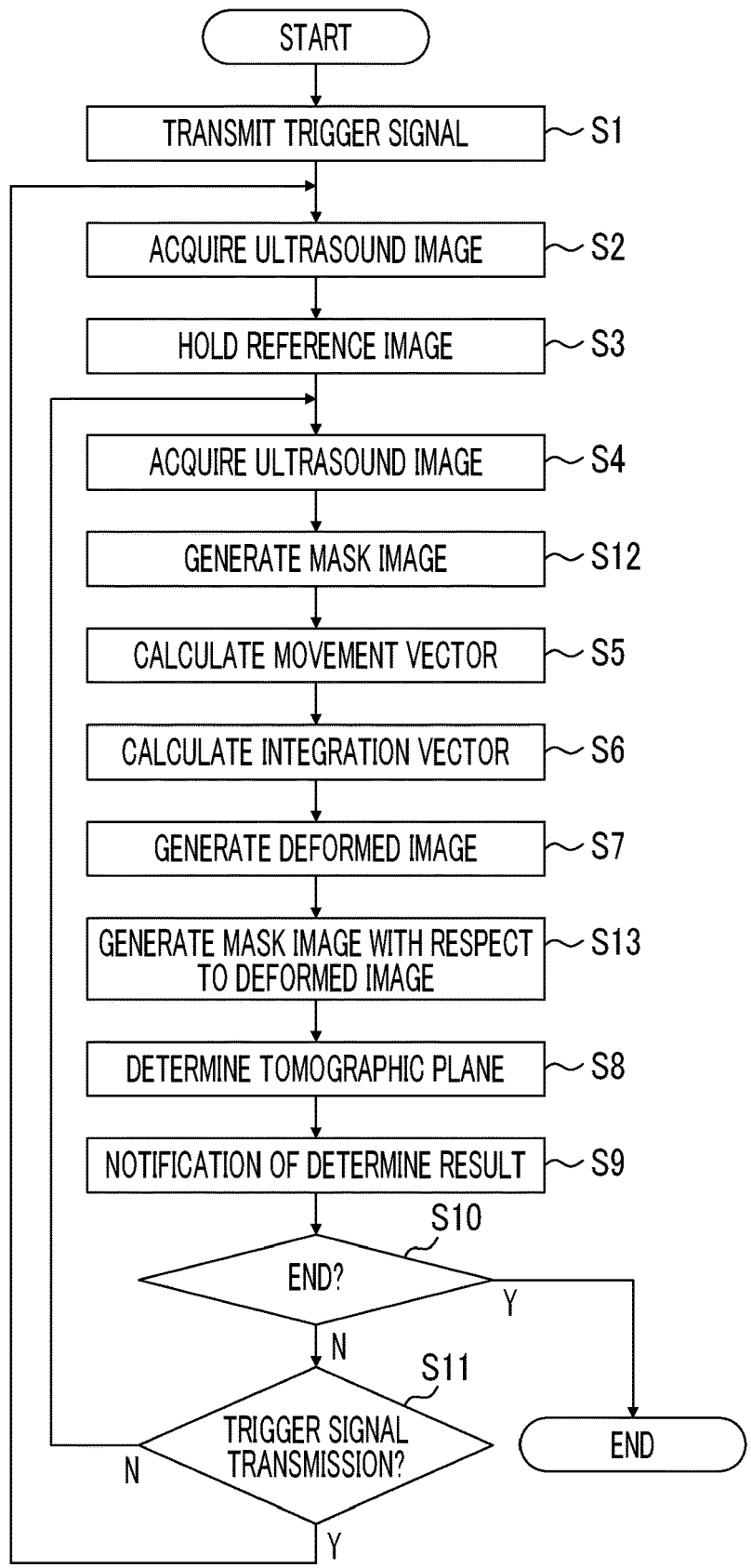
FIG. 12 is a flowchart illustrating the operation of the ultrasound diagnostic apparatus related to Embodiment 2 of the invention.

Next, the operation of the ultrasound diagnostic apparatus 1A of Embodiment 2 will be described using the flowchart illustrated in FIG. 12. A flowchart of FIG. 12 is provided by adding Step S12 between Step S4 and Step S5 and adding Step S13 between Step S7 and Step S8, in the flowchart of Embodiment 1 illustrated in FIG. 10.

First, in Step S1, in a case where the information indicating that a trigger signal is to be transmitted is input by the user via the input unit 17, the trigger signal transmitting unit 15 transmits the trigger signal to the reference image holding unit 9 and the movement vector integration unit 11.

In Step S2, the image acquisition unit 8 acquires an ultrasound image.

In the following Step S3, the reference image holding unit 9 holds the ultrasound image acquired in Step S2 as a reference image.

In Step S4, the image acquisition unit 8 acquires an ultrasound image similarly to Step S2.

In the following Step S12, the mask image generation unit 26 detects at least one of muscle fibers or a bone with respect to the ultrasound image acquired in Step S4, and generates a mask image C2 in which regions other than the detected muscle fibers and bone.

In Step S5, the movement vector calculation unit 10 calculates a movement vector indicating an image movement change between two ultrasound images by performing the image analysis with respect to the two ultrasound images of the ultrasound image acquired in Step S2, and the ultrasound image acquired in Step S4.

In Step S6, the movement vector integration unit 11 integrates the movement vector calculated in Step S5. At the current time, since the movement vector is calculated once in Step S5, an integration vector obtained in Step S6 is equal to the movement vector calculated in Step S5.

In Step S7, the deformed image generation unit 12 generates a deformed image in which the ultrasound image held as the reference image in Step S3 is deformed until the current time, on the basis of the movement change integrated in Step S6.

In Step S13, the mask image generation unit 26 detects at least one of muscle fibers or a bone with respect to the deformed image generated in Step S7 similarly to Step S12, and generates a mask image D2 in which regions other than the detected muscle fibers and bone are masked.

In Step S8, the tomographic plane determination unit 13 determines whether or not a tomographic plane of the subject depicted from the reference image and a tomographic plane of the subject depicted from the ultrasound image of the current frame are the same as each other by comparing the mask image C2 for the ultrasound image of the current frame generated in Step S12 with the mask image D2 with respect to the deformed image generated in Step S13.

In Step S9, the determination result notification unit 14 notifies the user of a determination result obtained in Step S8.

In Step S10, whether or not to end the operation of the ultrasound diagnostic apparatus 1A is determined. Here, in a case where it is determined that the operation of the ultrasound diagnostic apparatus 1A is not ended, the process proceeds to Step S11.

In Step S11, whether or not a trigger signal has been newly transmitted by the trigger signal transmitting unit 15 is determined. In a case where a trigger signal is not transmitted from the trigger signal transmitting unit 15 by the operation of the user via the input unit 17, it is determined that the trigger signal is not newly transmitted in Step S11, and the processing of Step S4, Step S5, Step S13, Step S6, Step S7, Step S13, and Step S8 to Step S11 is performed.

In a case where a trigger signal is transmitted from the trigger signal transmitting unit 15 to the reference image holding unit 9 and the movement vector integration unit 11 by the operation of the user via the input unit 17, it is determined that the trigger signal is newly transmitted in Step S11, and the process returns to Step S2.

In a case where the ultrasound image is newly acquired by the image acquisition unit 8 in Step S2, and the ultrasound image acquired by the reference image holding unit 9 in Step S2 is newly held as the reference image in Step S3, the processing of Step S4, Step S5, Step S13, Step S6, Step S7, Step S13, and Step S8 to Step S11 is performed again.

Additionally, in Step S10, in a case where it is determined that the operation of the ultrasound diagnostic apparatus 1A is ended, the operation of the ultrasound diagnostic apparatus 1A ends.

According to the ultrasound diagnostic apparatus 1A of Embodiment 2 as described above, the deformed image can be compared with the ultrasound image of the current frame while paying attention to at least one of muscle fibers or a bone in which a change of a structure pattern in an ultrasound image is particularly remarkable with respect to a change of a tomographic plane depicted from an ultrasound image by comparing the mask image C2 for the ultrasound image of the current frame and the mask image D2 for the deformed image. Therefore, determination of the tomographic planes can be more easily and accurately performed.

In addition, in Embodiment 2, the mask image generation unit 26 detects at least one of muscle fibers or a bone with respect to each of the deformed image and the ultrasound image of the current frame and generates the mask images C2 and D2 in which the regions other than the muscle fibers and the bone are masked. However, for example, the mask image generation unit 26 can generate the mask image C2 for the ultrasound image of the current frame by applying the same mask as the mask for the deformed image to the ultrasound image of the current frame instead of generating the mask for the ultrasound image of the current frame. Additionally, the mask image generation unit 26 can also generate, for example, the mask image D2 for the deformed image by applying the same mask as the mask for the ultrasound image of the current frame to the deformed image instead of generating the mask for the deformed image.

Additionally, in Embodiment 2, although the mask image generation unit 26 generates the mask images C2 and D2 in which the regions other than the detected muscle fibers and bone are masked, the mask images C2 and D2 are not limited to this. For example, also regarding the nerve bundle, in a case where a tomographic plane of the subject depicted from an ultrasound image changes, the structure pattern of the nerve bundle expressed by pixels with high luminance changes markedly. Therefore, the mask image generation unit 26 can generate the mask images C2 and D2 in which the nerve bundle is not masked. Although the mask image generation unit 26 detects the blood vessel and the nerve bundle using the Hessian matrix H in Embodiment 2, generally, the nerve bundle is depicted from pixels having a luminance higher than the blood vessel. Therefore, for example, the mask image generation unit 26 can detect a region of which the luminance is equal to or more than the threshold among the regions detected using the Hessian matrix H, as the nerve bundle. However, usually, there is a case where the region of the nerve bundle is smaller than the region of the muscle fibers and the bone, and is not clearly depicted depending on tomographic planes. Therefore, those obtained by masking the regions other than the muscle fibers and the bone are preferable as the mask images C2 and D2.

Additionally, in Embodiment 2, although the mask image generation unit 26 detects a region indicating a bone by measuring the luminance within an ultrasound image with a threshold, detects regions indicating a blood vessel, a nerve bundle, a tendon, and the like, and detects the remaining region as a region indicating muscle fibers, the method of detecting the bone and the muscle fibers is not particularly limited to this. For example, the mask image generation unit 26 can learn features of bones and muscle fibers using general image recognition techniques, such as a machine learning technique and deep learning, and can also detect regions indicating a bone and muscle fibers.

Embodiment 3

In Embodiment 2, although the mask image D2 is generated with respect to the deformed image generated by the deformed image generation unit 12, a mask image can also be generated with respect to all ultrasound images acquired by the image acquisition unit 8, and a movement vector can also be calculated with respect to the generated mask image.

Figure 13:
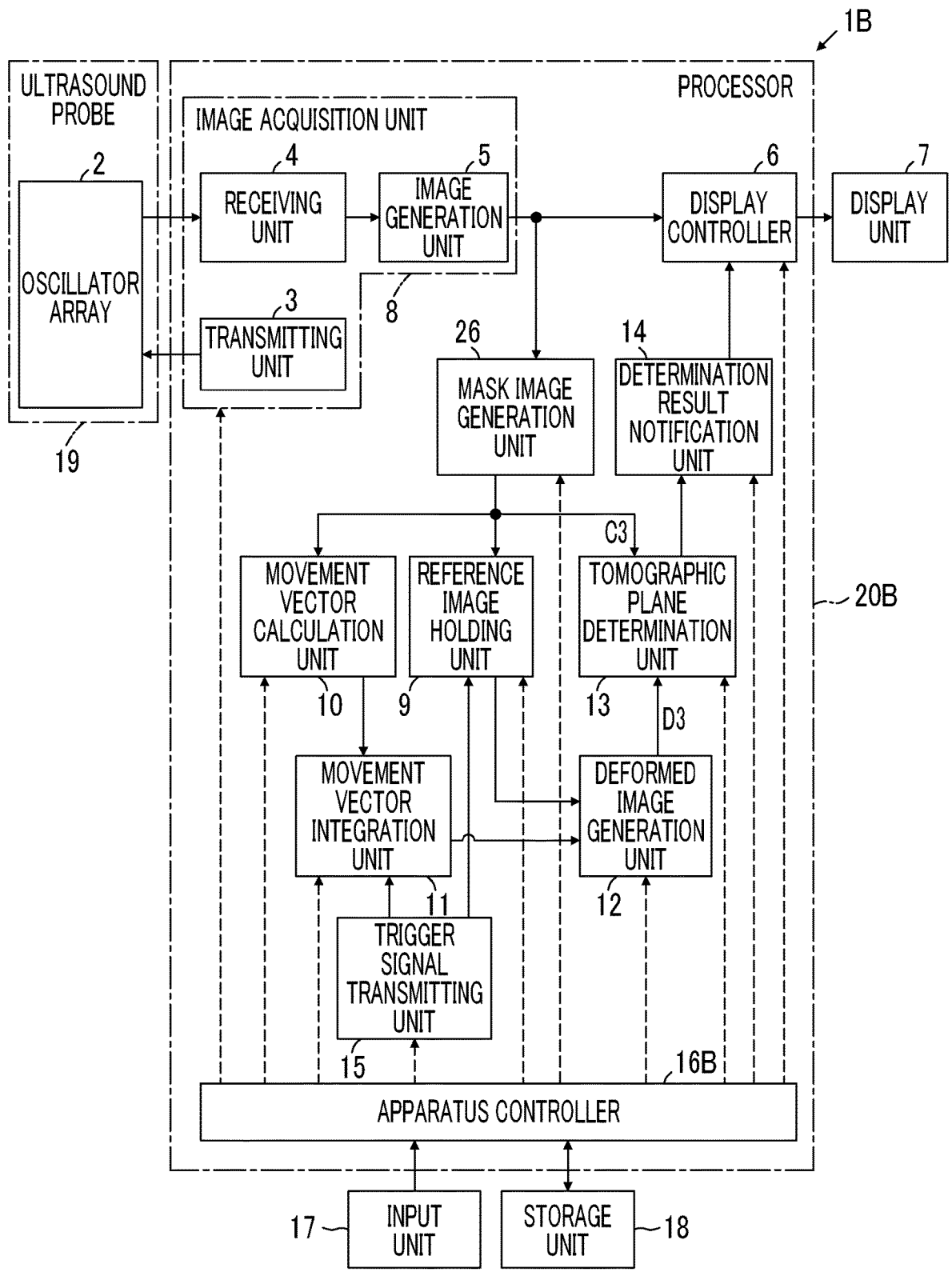
FIG. 13 is a block diagram illustrating the configuration of an ultrasound diagnostic apparatus related to Embodiment 3 of the invention.

The configuration of an ultrasound diagnostic apparatus 1B related to Embodiment 3 is illustrated in FIG. 13. The ultrasound diagnostic apparatus 1B of Embodiment 3 comprises an apparatus controller 16B instead of the apparatus controller 16A in the ultrasound diagnostic apparatus 1A of Embodiment 2 illustrated in FIG. 11, and the mask image generation unit 26 is connected to the movement vector calculation unit 10 instead of being directly connected to the deformed image generation unit 12.

In the ultrasound diagnostic apparatus 1B of Embodiment 3, the mask image generation unit 26 is connected to the image generation unit 5, and the reference image holding unit 9, the movement vector calculation unit 10, and the tomographic plane determination unit 13 are connected to the mask image generation unit 26. Additionally, the apparatus controller 16B is connected to the display controller 6, the image acquisition unit 8, the reference image holding unit 9, the movement vector calculation unit 10, the movement vector integration unit 11, the deformed image generation unit 12, the tomographic plane determination unit 13, the determination result notification unit 14, the trigger signal transmitting unit 15, and the mask image generation unit 26.

Moreover, a processor 20B is configured by the display controller 6, the image acquisition unit 8, the reference image holding unit 9, the movement vector calculation unit 10, the movement vector integration unit 11, the deformed image generation unit 12, the tomographic plane determination unit 13, the determination result notification unit 14, the trigger signal transmitting unit 15, the apparatus controller 16B, and the mask image generation unit 26.

Similarly to the mask image generation unit in Embodiment 2, the mask image generation unit 26 of the processor 20B detects at least one of muscle fibers or a bone with respect to a ultrasound image acquired by the image acquisition unit 8, and generates a mask image in which regions other than the muscle fibers and the bone are masked.

The reference image holding unit 9 of the processor 20B holds the mask image generated by the mask image generation unit 26 as a reference image.

The movement vector calculation unit 10 of the processor 20B calculates a movement vector indicating an image movement change with respect to two consecutive mask images generated by the mask image generation unit 26.

The movement vector integration unit 11 of the processor 20B integrates the movement vector calculated by the movement vector calculation unit 10.

The deformed image generation unit 12 of the processor 20B generates a deformed image D3 in which the mask image held by the reference image holding unit 9 is deformed until the current time, on the basis of the integrated movement change integrated by the movement vector integration unit 11.

As illustrated in FIG. 13, the tomographic plane determination unit 13 of the processor 20B determines whether or not a tomographic plane of the subject depicted from the reference image and a tomographic plane of the subject depicted from the ultrasound image of the current frame are the same as each other by comparing the deformed image D3 generated by the deformed image generation unit 12 with the mask image C3 generated with respect to the ultrasound image of the current frame by the mask image generation unit 26.

Figure 14:
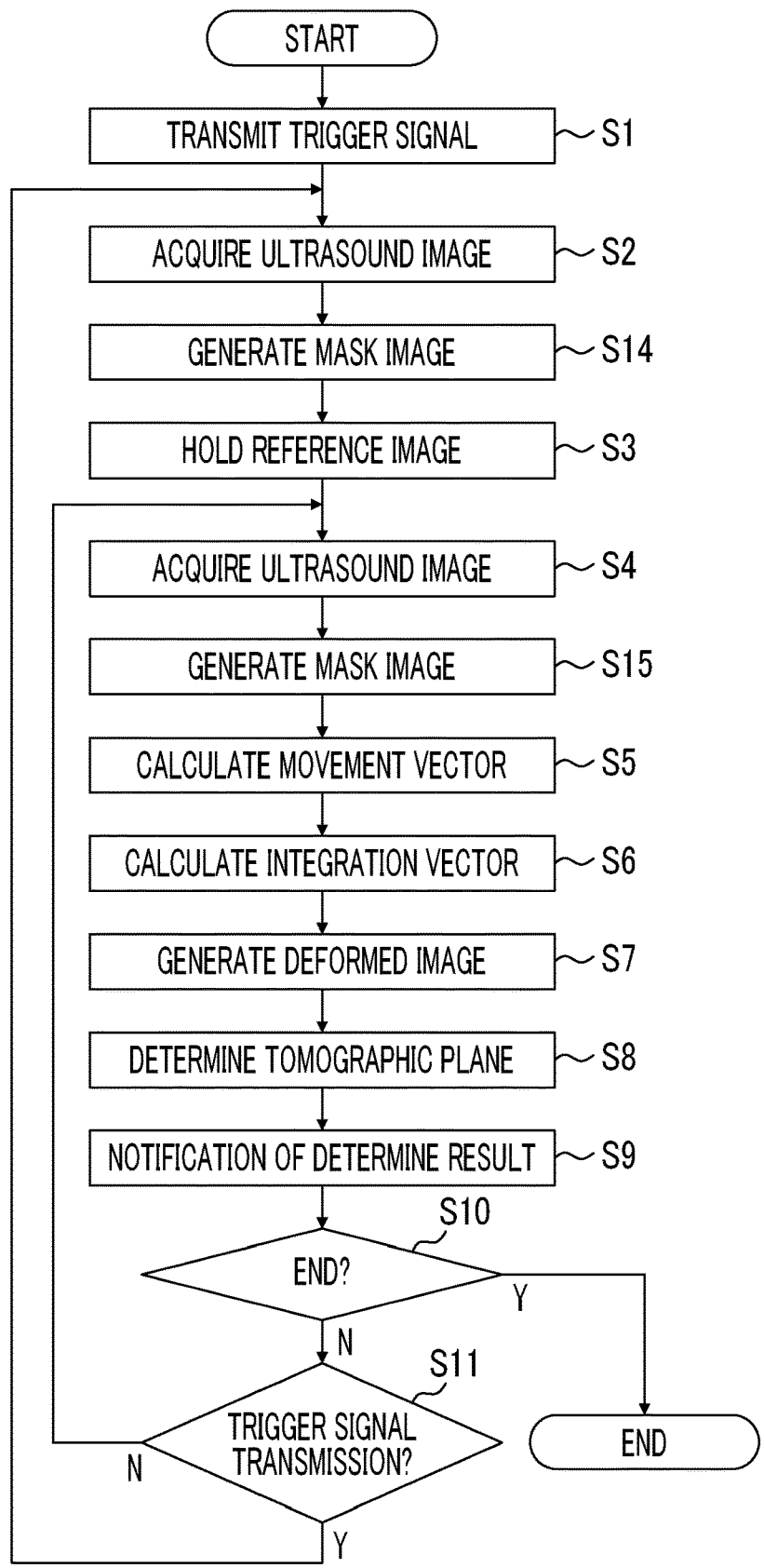
FIG. 14 is a flowchart illustrating the operation of the ultrasound diagnostic apparatus related to Embodiment 3 of the invention.

Next, the operation of the ultrasound diagnostic apparatus 1B of Embodiment 3 will be described using a flowchart of FIG. 14. A flowchart of FIG. 14 is provided by adding Step S14 between Step S2 and Step S3 and adds Step S15 between Step S4 and Step S5, in the flowchart of Embodiment 1 illustrated in FIG. 10.

First, in Step S1, in a case where the information indicating that a trigger signal is to be transmitted is input by the user via the input unit 17, the trigger signal transmitting unit 15 transmits the trigger signal to the reference image holding unit 9 and the movement vector integration unit 11.

In Step S2, the image acquisition unit 8 acquires an ultrasound image.

In the following Step S14, the mask image generation unit 26 detects at least one of muscle fibers or a bone with respect to the ultrasound image acquired in Step S2, and generates a mask image in which regions other than the muscle fibers and the bone are masked.

In Step S3, the reference image holding unit 9 holds the mask image generated in Step S14 as a reference image.

In Step S4, the image acquisition unit 8 acquires an ultrasound image similarly to Step S2.

In Step S15, the mask image generation unit 26 generates a mask image with respect to the ultrasound image acquired in Step S4 similarly to Step S14.

In Step S5, the movement vector calculation unit 10 calculates a movement vector indicating an image movement change between two mask images by performing image analysis with respect to the two mask images of the mask image generated in Step S14 and the mask image generated in Step S15.

In Step S6, the movement vector integration unit 11 integrates the movement vector calculated in Step S5. At the current time, since the movement vector is calculated once in Step S5, the integration vector obtained in Step S6 is equal to the movement vector calculated in Step S5.

In Step S7, the deformed image generation unit 12 generates a deformed image in which the ultrasound image held as the reference image in Step S3 is deformed until the current time, on the basis of the movement change integrated in Step S6.

In Step S8, the tomographic plane determination unit 13 determines whether or not a tomographic plane of the subject depicted from the reference image and a tomographic plane of the subject depicted from the ultrasound image of the current frame are the same as each other By comparing the mask image C3 for the ultrasound image of the current frame generated in Step S15 with the deformed image D3 generated in Step S7.

In Step S9, the determination result notification unit 14 notifies the user of a determination result obtained in Step S8.

In Step S10, whether or not to end the operation of the ultrasound diagnostic apparatus 1B is determined. Here, in a case where it is determined that the operation of the ultrasound diagnostic apparatus 1B is not ended, the process proceeds to Step S11.

In Step S11, whether or not a trigger signal has been newly transmitted by the trigger signal transmitting unit 15 is determined. In a case where a trigger signal is not transmitted from the trigger signal transmitting unit 15 by the operation of the user via the input unit 17, it is determined that the trigger signal is not newly transmitted in Step S11, and the processing of Step S4, Step S15, and Step S5 to Step S11 is performed. In a case where a trigger signal is transmitted from the trigger signal transmitting unit 15 to the reference image holding unit 9 and the movement vector integration unit 11 by the operation of the user via the input unit 17, it is determined that the trigger signal is newly transmitted in Step S11, and the process returns to Step S2.

In a case where an ultrasound image is newly acquired by the image acquisition unit 8 in Step S2, a mask image for the ultrasound image acquired in Step S2 is generated by the mask image generation unit 26 in Step S14.

In the following Step S3, in a case where the mask image generated by the reference image holding unit 9 in Step S14 is newly held as the reference image, the processing of Step S4, Step S15, and Step S5 to Step S11 is performed again.

Additionally, in Step S10, in a case where it is determined that the operation of the ultrasound diagnostic apparatus 1B is ended, the operation of the ultrasound diagnostic apparatus 1B is ended.

As described above, according to the ultrasound diagnostic apparatus 1B of Embodiment 3, similarly to the ultrasound diagnostic apparatus 1A of Embodiment 2, the deformed image can be compared with the ultrasound image of the current frame while paying attention to at least one of muscle fibers or a bone in which a change of a structure pattern in an ultrasound image is particularly remarkable with respect to a change of a tomographic plane depicted from an ultrasound image. Therefore, determination of the tomographic planes can be more easily and accurately performed.

Embodiment 4

In Embodiment 1 to Embodiment 3, the trigger signal transmitting unit 15 transmits a trigger signal to the reference image holding unit 9 and the movement vector integration unit 11 by inputting the information indicating that the trigger signal is to be transmitted by the user via the input unit 17, the trigger signal can also automatically be transmitted.

Figure 15:
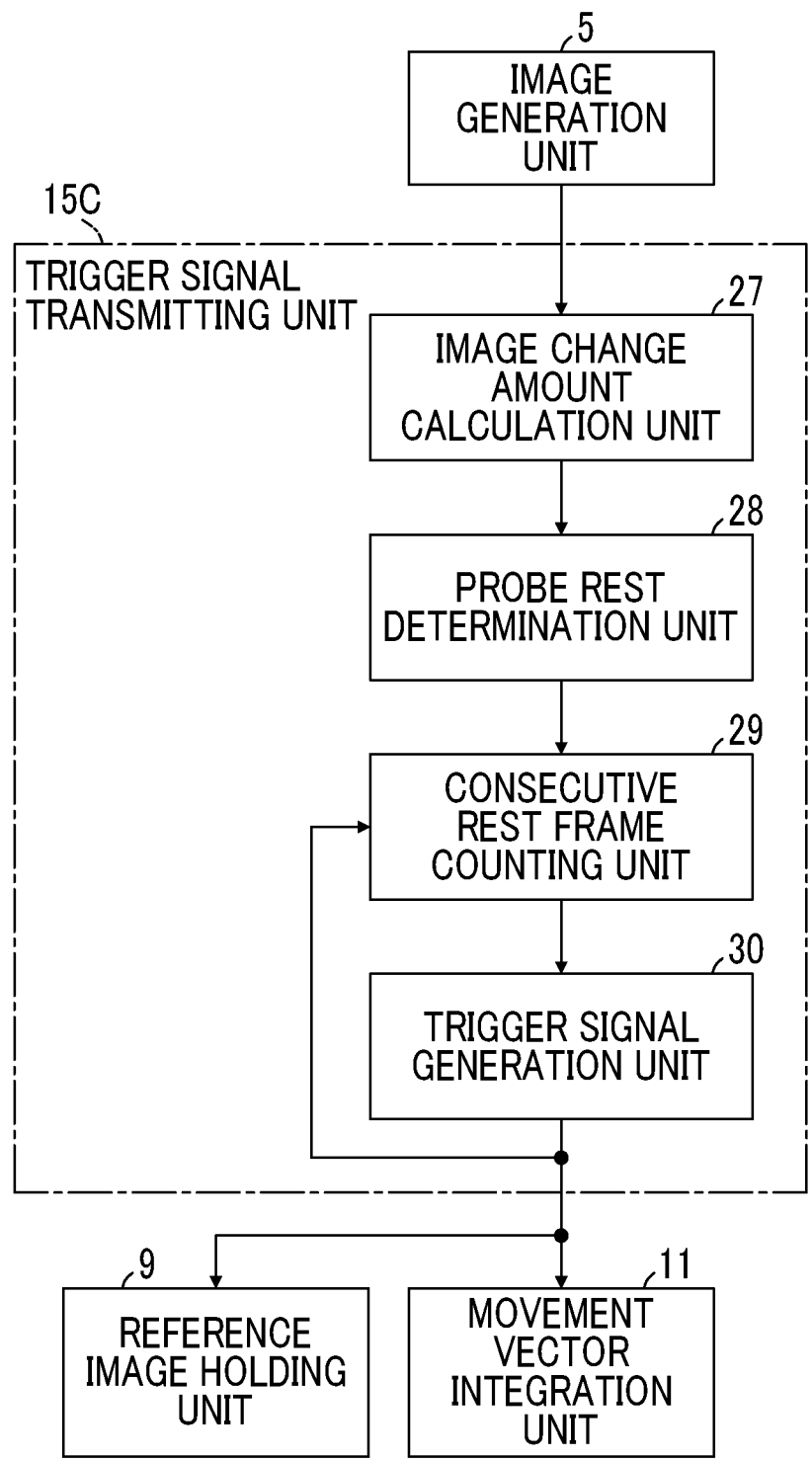
FIG. 15 is a block diagram illustrating an internal configuration of the trigger signal transmitting unit in Embodiment 4.

An internal configuration of the trigger signal transmitting unit 15C in Embodiment 4 is illustrated in FIG. 15. As illustrated in FIG. 15, the trigger signal transmitting unit 15C has a configuration in which an image change amount calculation unit 27, a probe rest determination unit 28, a consecutive rest frame counting unit 29, and a trigger signal generation unit 30 are connected in series. Additionally, the image change amount calculation unit 27 is connected to the image generation unit 5. Additionally, the trigger signal generation unit 30 is connected to the consecutive rest frame counting unit 29 in both directions. Moreover, the trigger signal generation unit 30 is connected to the reference image holding unit 9 and the movement vector integration unit 11.

The trigger signal transmitting unit 15C performs image analysis with respect to ultrasound images sequentially acquired by the image acquisition unit 8 to determine whether or not the ultrasound probe 19 is at rest, and automatically transmits a trigger signal to the reference image holding unit 9 and the movement vector integration unit 11 for example, in a case where the ultrasound probe 19 is consecutive at rest only by the time corresponding to a determined number of frames of 15 frames to 30 frames.

Here, in a case where the compression test of the subject is performed, usually, the user positions the ultrasound probe 19, and then presses the ultrasound probe 19 against the body surface of the subject to start the compression test. Moreover, in a case where the ultrasound probe 19 is positioned, there are many cases where the user makes the ultrasound probe 19 at rest. Therefore, a trigger signal is automatically transmitted to the reference image holding unit 9 and the movement vector integration unit 11 by the trigger signal transmitting unit 15C at a timing when the compression test is started.

The image change amount calculation unit 27 of the trigger signal transmitting unit 15C calculates the image change amount between two ultrasound images by performing image analysis with respect to the two consecutive ultrasound images generated by the image generation unit 5. Here, the image change amount is an index indicating how much images have changed, and a distance at which the images have moved between the two ultrasound images, an angle at which the images has rotated, or the like can be used.

The probe rest determination unit 28 of the trigger signal transmitting unit 15C determines whether or not the ultrasound probe 19 is at rest on the basis of the image change amount calculated by the image change amount calculation unit 27. For example, the probe rest determination unit 28 determines that the ultrasound probe 19 is at rest in a case where the image change amount calculated by the image change amount calculation unit 27 is equal to or less than a threshold, and is determined that the ultrasound probe 19 is moving in a case where the image change amount is larger than the threshold.

In a case it is determined that the ultrasound probe is moving by the probe rest determination unit 28, the image change amount is newly calculated by the image change amount calculation unit 27 with respect to an ultrasound image newly generated by the image generation unit 5 and the determination caused by the probe rest determination unit 28 is performed on the basis of the calculated image change amount.

The consecutive rest frame counting unit 29 of the trigger signal transmitting unit 15C counts the number of consecutive ultrasound image frames by which the probe rest determination unit 28 has determined that the ultrasound probe 19 is at rest.

In a case where the number of frames counted by the consecutive rest frame counting unit 29 reaches a predetermined number of frames, the trigger signal generation unit 30 of the trigger signal transmitting unit 15C generates a trigger signal, and transmits the generated trigger signal to the reference image holding unit 9, the movement vector integration unit 11, and the consecutive rest frame counting unit 29. In this way, in a case where a trigger signal is transmitted from the trigger signal generation unit 30, the reference image holding unit 9 eliminates the reference image held until now, the movement vector integration unit 11 eliminates the held integration vector, and the consecutive rest frame counting unit 29 eliminates the counted number of frames.

As described above, according to the ultrasound diagnostic apparatus related to Embodiment 4, the trigger signal transmitting unit 15C automatically transmits a trigger signal in a case where the ultrasound probe 19 is consecutively at rest by a determined number of times. Therefore, the trigger signal is transmitted at a timing when the compression test is started, and the user's labor in the compression test can be mitigated.

In addition, the trigger signal transmitting unit 15C in Embodiment 4 is applicable to the ultrasound diagnostic apparatuses 1, 1A, and 1B of Embodiments 1 to 3.

EXPLANATION OF REFERENCES 1, 1A, 1B: ultrasound diagnostic apparatus
2: oscillator array
3: transmitting unit
4: receiving unit
5: image generation unit
6: display controller
7: display unit
8: image acquisition unit
9: reference image holding unit
10: movement vector calculation unit
11: movement vector integration unit
12: deformed image generation unit
13: tomographic plane determination unit
14: determination result notification unit
15, 15C: trigger signal transmitting unit
16, 16A, 16B: apparatus controller
17: input unit
18: storage unit
19: ultrasound probe
20, 20A, 20B: processor
21: amplification unit
22: AD conversion unit
23: signal processing unit
24: DSC
25: image processing unit
26: mask image generation unit
27: image change amount calculation unit
28: probe rest determination unit
29: consecutive rest frame counting unit
30: trigger signal generation unit
B: bone
BS: body surface
BV: blood vessel
C1: ultrasound image of current frame
D1, D3: deformed image
FP1, FP2: tomographic plane
C2, D2, C3: mask image
MF: muscle fiber
R1, R2, R3: region
U1, U2, U3, U4: ultrasound image

What is claimed is:

1. An ultrasound diagnostic apparatus that has an ultrasound probe and is used to compression-test an observation target within a subject by pressing the ultrasound probe against a body surface of the subject, the ultrasound diagnostic apparatus comprising:

a processor; and
a monitor,
wherein the processor is configured to
perform transmission of an ultrasound beam from the ultrasound probe toward the subject and acquires ultrasound images consecutively and sequentially;
display the ultrasound image acquired;
hold the ultrasound image acquired as a reference image in a state where a position of the ultrasound probe is fixed in order to depict a tomographic plane of the observation target on the monitor;
calculate a movement vector indicating an image movement change between two ultrasound images that are consecutive for each predetermined number of frames among the ultrasound images sequentially acquired;
integrate the movement vectors that are respectively calculated in the ultrasound images from the time when the reference image is held until the current time;
a generate a deformed image in which the ultrasound image held as the reference image is moved and changed until the current time on the basis of the movement change integrated;
determine whether or not a tomographic plane of the subject depicted from the reference image and a tomographic plane of the subject depicted from the ultrasound image of the current frame are the same as each other by comparing the deformed image generated with the ultrasound image of the current frame acquired; and
notify a user of a determination result.

2. The ultrasound diagnostic apparatus according to claim 1,
wherein the processor is configured to calculate a movement change of each pixel in the ultrasound image as the movement vector.

3. The ultrasound diagnostic apparatus according to claim 2,
wherein the processor is configured to integrate the movement vector for each pixel with respect to the ultrasound images of a plurality of frames acquired, and
generate the deformed image by moving and changing each pixel in the reference image until the current time in accordance with the movement change integrated.

4. The ultrasound diagnostic apparatus according to claim 1,
wherein the processor is configured to calculate a movement change of a high-luminance pixel of which a luminance is equal to or more than a predetermined threshold, among all pixels in the ultrasound image, as the movement vector.

5. The ultrasound diagnostic apparatus according to claim 4,
wherein the processor is configured to integrate the movement vector for each high-luminance pixel with respect to the ultrasound images of a plurality of frames acquired, and
generate the deformed image on the basis of a movement change of each high-luminance pixel in the reference image.

6. The ultrasound diagnostic apparatus according to claim 1,
wherein the processor is configured to partition the ultrasound images adjacent to each other in time series into a predetermined number of regions, respectively, and calculates a movement change of one pixel in each of the regions as the movement vector of the region.

7. The ultrasound diagnostic apparatus according to claim 6, wherein the processor is configured to integrate the movement vector for each of the regions partitioned in the ultrasound images of the plurality of frames acquired, and generate the deformed image on the basis of a movement change of each region in the reference image.

8. The ultrasound diagnostic apparatus according to claim 7, wherein the processor is configured to compare the deformed image with the ultrasound image of the current frame for each of the regions partitioned, to determine the tomographic planes of the subject, and notify the user of the determination result for each partitioned region.

9. The ultrasound diagnostic apparatus according to claim 1, wherein the processor is configured to perform image analysis with respect to the deformed image and the ultrasound image of the current frame, to calculate a similarity between the deformed image and the ultrasound image of the current frame, and determine the tomographic planes of the subject on the basis of the calculated similarity.

10. The ultrasound diagnostic apparatus according to claim 2, wherein the processor is configured to perform image analysis with respect to the deformed image and the ultrasound image of the current frame, to calculate a similarity between the deformed image and the ultrasound image of the current frame, and determine the tomographic planes of the subject on the basis of the calculated similarity.

11. The ultrasound diagnostic apparatus according to claim 3, wherein the processor is configured to perform image analysis with respect to the deformed image and the ultrasound image of the current frame, to calculate a similarity between the deformed image and the ultrasound image of the current frame, and determine the tomographic planes of the subject on the basis of the calculated similarity.

12. The ultrasound diagnostic apparatus according to claim 1, wherein the processor is configured to superimpose the determination result on the ultrasound image of the current frame to display the superimposed image on the monitor.

13. The ultrasound diagnostic apparatus according to claim 1, wherein the process is configured to perform image analysis with respect to the deformed image generated, and the ultrasound image of the current frame acquired to detect at least one of muscle fibers or a bone, and generate a mask image in which regions other than the muscle fibers and the bone detected with respect to the deformed image and the ultrasound image of the current frame are masked.

14. The ultrasound diagnostic apparatus according to claim 13, wherein the processor is configured to determine the tomographic planes of the subject by comparing the mask image for the deformed image and the mask image for the ultrasound image of the current frame.

15. The ultrasound diagnostic apparatus according to claim 1, wherein the processor is configured to perform image analysis with respect to the ultrasound images, which are consecutively and sequentially acquired to detect at least one of muscle fibers or a bone, generate a mask image in which regions other than the muscle fibers and the bone detected with respect to the ultrasound image are masked, hold the mask image generated at the time when the position of the ultrasound probe is fixed in order to depict a tomographic plane of the observation target on the monitor, as the reference image, calculate an image movement change in the mask image as the movement vector, and generate a deformed image in which the mask image held as the reference image is moved and changed until the current time on the basis of a movement change of at least one of the muscle fibers or the bone integrated.

16. The ultrasound diagnostic apparatus according to claim 15, wherein the processor is configured to determine a tomographic plane of the subject by comparing the deformed image with a mask image that is masked with respect to the ultrasound image of the current frame.

17. The ultrasound diagnostic apparatus according to claim 1, further comprising:

an input device that allows a user to perform an input operation, wherein the processor is configured to transmit a trigger signal in a case where information indicating that the trigger signal instructing to start a new operation is transmitted is input by the user via the input device.

18. The ultrasound diagnostic apparatus according to claim 1, wherein the processor is configured to perform image analysis with respect to the ultrasound images acquired consecutively and sequentially to calculate an image change amount that is at least one of an image movement distance between two consecutive ultrasound images or a rotational amount between the two consecutive ultrasound images, and transmit a trigger signal instructing to start a new operation in a case where the ultrasound images of which the image change amount is equal to or less than a predetermined threshold are consecutively acquired by a predetermined number of frames.

19. The ultrasound diagnostic apparatus according to claim 1, wherein the monitor displays the deformed image side by side with the ultrasound image of the current frame.

* * * * *